United States Patent
Thompson et al.

(10) Patent No.: US 10,401,325 B2
(45) Date of Patent: Sep. 3, 2019

(54) MAGNETIZERS FOR PIGGING TOOLS

(71) Applicant: Novitech Inc., Denver, CO (US)

(72) Inventors: Ron Thompson, Vaughan (CA); Calin Cristian Ganea, Toronto (CA)

(73) Assignee: Novitech, Inc., Denver, CO (US)

(*) Notice: Subject to any disclaimer, the term of this patent is extended or adjusted under 35 U.S.C. 154(b) by 51 days.

(21) Appl. No.: 15/674,973

(22) Filed: Aug. 11, 2017

(65) Prior Publication Data

US 2018/0045680 A1   Feb. 15, 2018

Related U.S. Application Data

(60) Provisional application No. 62/373,902, filed on Aug. 11, 2016, provisional application No. 62/448,811, filed on Jan. 20, 2017.

(51) Int. Cl.
*G01N 27/82* (2006.01)

(52) U.S. Cl.
CPC .................. *G01N 27/82* (2013.01)

(58) Field of Classification Search
CPC .......... G01N 27/82; G01N 27/83; G01N 27/85
See application file for complete search history.

(56) References Cited

U.S. PATENT DOCUMENTS

| | | | | |
|---|---|---|---|---|
| 3,899,734 A | * | 8/1975 | Beaver | G01M 3/005 324/220 |
| 3,949,292 A | * | 4/1976 | Beaver | G01M 3/005 324/220 |
| 4,105,972 A | * | 8/1978 | Smith | G01M 3/005 324/220 |
| 5,454,276 A | * | 10/1995 | Wernicke | G01N 27/82 324/220 |
| 5,864,232 A | | 1/1999 | Laursen | |

(Continued)

FOREIGN PATENT DOCUMENTS

| CA | 2541740 | 5/1998 |
|---|---|---|
| CA | 2941509 | 12/2010 |

OTHER PUBLICATIONS

International Search Report and Written Opinion issued in Parent PCT Application No. PCT/IB2018/050330, dated Apr. 17, 2018.

*Primary Examiner* — Clayton E. LaBalle
*Assistant Examiner* — Milton Gonzalez
(74) *Attorney, Agent, or Firm* — BakerHostetler

(57) ABSTRACT

Circumferential and axial magnetizers for a magnetic flux leakage pig. A circumferential magnetizer module for a smart pig comprises a central shaft and at least one magnet bar for inducing a magnetic field transverse to a longitudinal axis of the shaft. The magnet bar comprises at least one magnet, and may collapse radially inward to the shaft. A sensor head disposed between circuit poles at each polar end of the magnet monitors magnetic flux. An axial magnetizer module comprises a central shaft and at least one magnet bar to induce a magnetic field coaxially to a longitudinal axis of the shaft. Magnets of opposite polarity are circumferentially disposed around ends of the central shaft. A sensor head disposed between circuit poles at each polar end monitors magnetic flux. The central shaft of a circumferential magnetizer or axial magnetizer may comprise a joint linking an additional smart pig module.

16 Claims, 19 Drawing Sheets

(56) References Cited

U.S. PATENT DOCUMENTS

| | | | |
|---|---|---|---|
| 6,023,986 A * | 2/2000 | Smith | G01C 7/06 |
| | | | 324/220 |
| 6,198,277 B1 | 3/2001 | Porter et al. | |
| 6,538,431 B2 * | 3/2003 | Couchman | F16L 55/28 |
| | | | 15/104.061 |
| 6,640,655 B1 | 11/2003 | Manzak et al. | |
| 6,762,602 B1 | 7/2004 | Laursen et al. | |
| 6,847,207 B1 | 1/2005 | Veach et al. | |
| 6,924,640 B2 | 8/2005 | Flickert et al. | |
| 7,038,444 B2 | 5/2006 | Crouch et al. | |
| 7,218,102 B2 | 5/2007 | Nestleroth et al. | |
| 7,402,999 B2 | 7/2008 | Plotnikov et al. | |
| 7,458,289 B2 | 12/2008 | Houldey et al. | |
| 7,548,059 B2 | 6/2009 | Thompson et al. | |
| 7,595,636 B2 | 9/2009 | Barolak et al. | |
| 7,859,256 B1 * | 12/2010 | Hoyt | G01N 27/87 |
| | | | 324/220 |
| 7,923,994 B2 | 4/2011 | Hoyt | |
| 8,035,374 B1 * | 10/2011 | Girrell | E21B 47/0905 |
| | | | 324/303 |
| 8,232,796 B2 | 7/2012 | Laursen et al. | |
| 8,653,811 B2 | 2/2014 | Simek et al. | |
| 8,674,678 B2 | 3/2014 | Hwang et al. | |
| 8,797,033 B1 * | 8/2014 | Girrell | E21B 47/0006 |
| | | | 324/309 |
| 9,442,126 B2 | 9/2016 | Laursen et al. | |
| 9,625,418 B2 | 4/2017 | Laursen et al. | |
| 9,728,817 B2 | 8/2017 | Comello et al. | |
| 2009/0166035 A1 * | 7/2009 | Almaguer | E21B 7/061 |
| | | | 166/254.1 |
| 2010/0327859 A1 | 12/2010 | Simek et al. | |
| 2012/0176127 A1 | 7/2012 | Fussell et al. | |

* cited by examiner

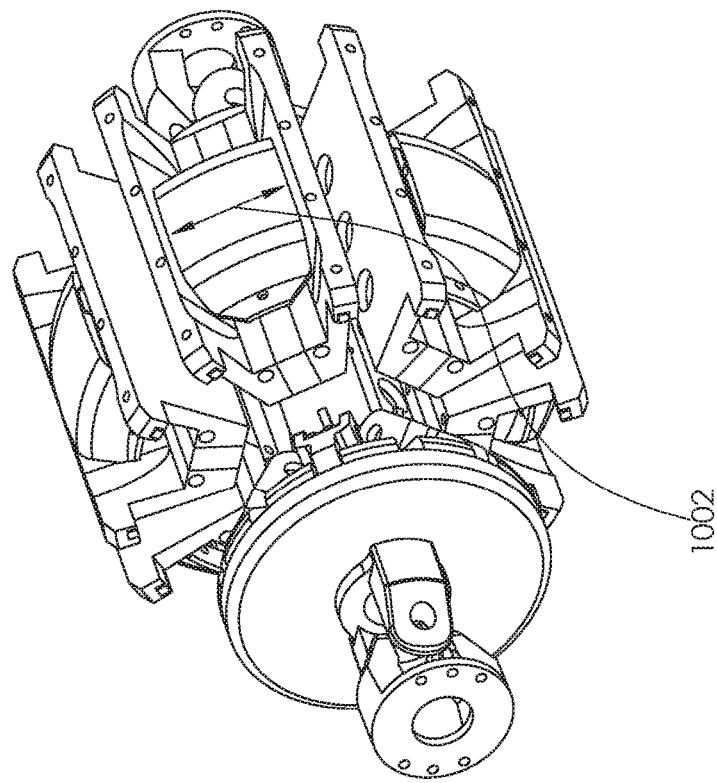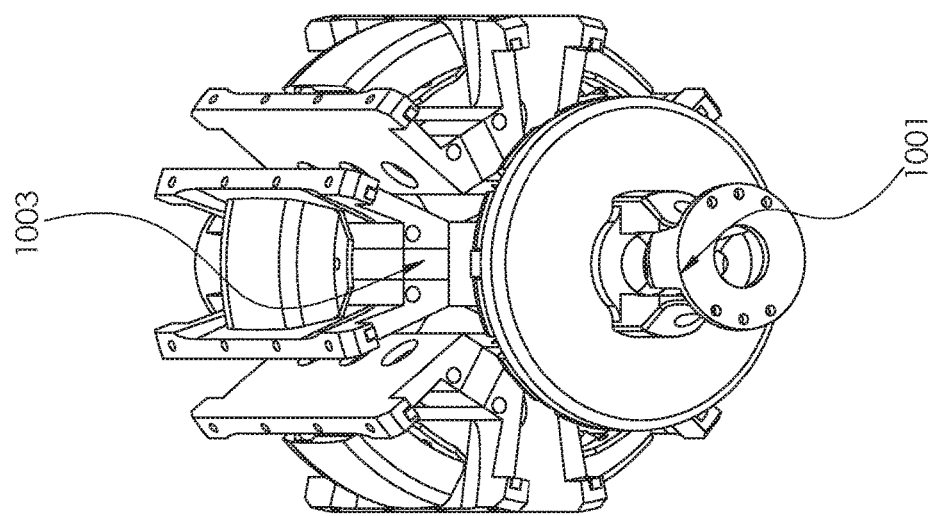
FIG. 10

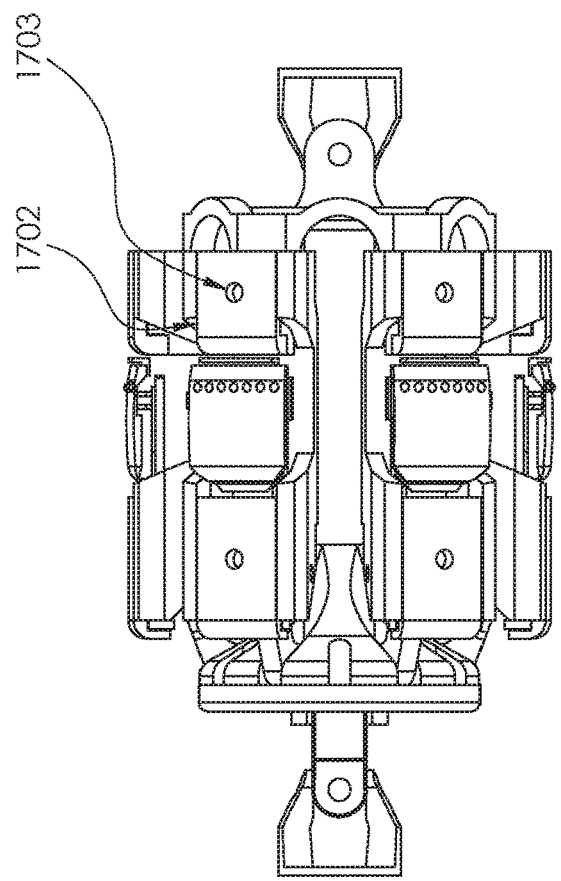
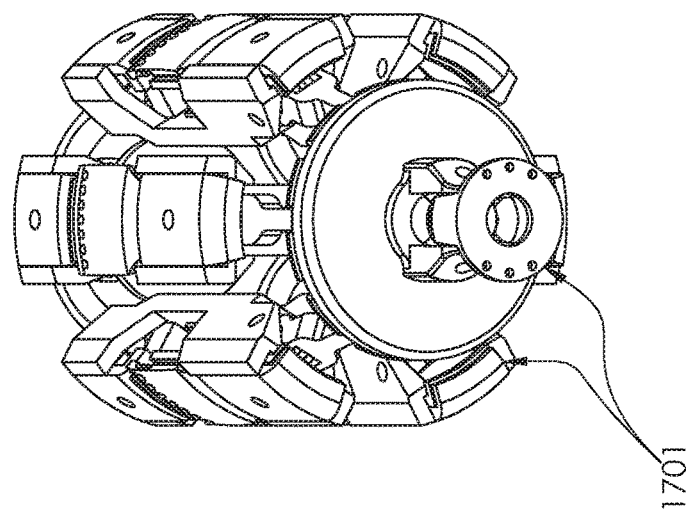
FIG. 17

MAGNETIZERS FOR PIGGING TOOLS

CROSS-REFERENCE

This application claims benefit under 35 U.S.C. § 119(e) of Provisional U.S. Patent Application No. 62/373,902, filed Aug. 11, 2016 and Provisional U.S. Patent Application No. 62/448,811, filed Jan. 20, 2017, the contents of which is incorporated herein by reference in its entirety.

TECHNICAL FIELD

The present disclosure relates to apparatus and systems for inspecting pipelines. More specifically, the present disclosure relates to apparatus and systems for detecting structural defects, flaws, and other damage in pipeline systems.

BACKGROUND

The energy infrastructure of the world depends on pipelines. Pipelines transport crude oil and unrefined gas from wells to refineries and transport refined products to chemical plants, utilities, local distribution units, homes, airports, and nearly every place that uses energy. Energy pipelines include liquid petroleum pipelines and natural gas pipelines.

Pipelines can vary in size depending on purpose. For example, in oil-producing locations, gathering pipelines may be as small as two inches in diameter. The Trans-Alaska Pipeline, in contrast, which transports crude oil, is about 48 inches in diameter. Pipelines of varying sizes and purposes have diameters in between.

Given the materials being transported, pipelines present health, safety, environmental, and security concerns. Pipeline and energy companies are economically incentivized to bring as much product as possible from source to destination. The various governments also regulate pipelines and pipeline-transported materials extensively. To prevent release of pipeline-transported materials, pipeline and energy companies conduct integrity management programs continuously.

Integrity management programs include inspections to determine the integrity of pipeline systems. To this end, inspections may identify early indications of future problems, such as corrosion, cracks, mechanical damage, and dent and bend strain locations that may have defects that can cause failures in the future. Pipeline inspection companies have developed specialized tools to inspect the full body of pipelines, including inline inspection tools commonly referred to as smart pigs.

Smart pigs travel through the interior of a pipeline, often without stopping the flow of medium through the pipeline. These pigs may collect gigabytes of data about a pipeline including wall thickness, geometrical shape, corrosion, pitting, cracks, holes, dents, and other potential sources of problems. Identifiable flaws include, but are not limited to, metal loss caused by corrosion, erosion, pipe manufacturing, and construction of pipelines. These flaws may also include some forms of axially oriented flaws, such as narrow axial metal loss, hook cracks, lack of fusion, and fatigue-related cracking. These flaws may also include circumferentially oriented flaws of a similar nature. Mechanical damage may also be identified, including dents, gouges, cracks, and combined defects (e.g., a gouge near a pipe seam), and these types of damage may also be oriented either axially or circumferentially. Pigs use various, specialized sensing systems to automatically and continuously collect and store this data. Related software is typically used to interpret the data and aid operators in identifying significant flaws in order to investigate and make the necessary repairs to help prevent failures.

Pigs used for in-line inspection of pipelines may employ one or more of several technologies, including but not limited to ultrasonic technology ("UT") for wall thickness measurements or crack detection, electromagnetic acoustic transducer ("EMAT") technology, magnetic flux leakage ("MFL") technology, pipe surface profiling commonly referred to as geometry or caliper technology, and inertial mapping of pipe locations and detection of ground movement ("IMU"). MFL is a nondestructive method of testing that employs a magnetic flux leakage principle to detect certain defects and potential problems found in the full body of a pipeline. MFL can be used only in pipelines made of ferromagnetic metals, such as carbon based steels. Powerful magnets, including permanent or electromagnets, magnetize portions of the pipeline, and sensors may be generally placed between the poles of the magnets to monitor the changes in flux leakage from the pipeline in areas experiencing various flaws where the cross sectional area is reduced by metal loss or where a fissure or crack perpendicular to the direction of the magnetic field causes a detectable change in the magnetic leakage field. Automated feature searches and human analysis can provide comprehensive reporting, prioritizing, and quantifying the severity of flaws. This information is then used by the pipeline operators to facilitate field investigations, repairs, and future inspection intervals.

SUMMARY

The present disclosure relates to pigs utilizing magnetic flux leakage technology. An embodiment of the present disclosure relates to MFL pigs having one or more circumferential magnetizers. Another embodiment of the present disclosure relates to MFL pigs having one or more axial magnetizers. Yet another embodiment of the present disclosure relates to MFL pigs having at least one of a circumferential magnetizer and at least one of an axial magnetizer.

A pig may be cylindrical in shape and sized to fit the diameter of the pipeline being inspected. A pig may include one or more component bodies. Where a pig includes two or more component bodies, the component bodies may be operatively connected. For example, an MFL pig may include three or more component bodies operatively connected to each other, two or more of the component bodies including magnetizers comprising magnets and sensors, and another component body including batteries, data storage, and various electronics. In some embodiments, a pig may include more than three component bodies. For example, a pig may include three circumferential magnetizers, an axial magnetizer, an electronics body, a geometry body, an IMU body, and a battery body. In an embodiment, the axial or circumferential magnetizers may be offset from each other to provide complete circumferential sensor coverage of the pipe.

A magnetizer on an MFL pig may use permanent magnets or electromagnets. In an embodiment, a magnetizer may use rare-earth magnets, for example neodymium-based magnets. Rare-earth magnets, such as neodymium-based magnets, may be plated with a metal layer. For example, neodymium-based magnets may be plated with a thin nickel layer.

In an embodiment, each magnetizer module may be arranged with four or more magnet bars. In an embodiment, each magnetizer module may be arranged with six magnet bars. Each magnet bar may provide a localized circuit to bring the magnetic flux density in the pipe wall to near saturation levels. For example, the flux density in the pipe wall may be brought equal to or greater than 1.6 Tesla. One of skill in the art will recognize that the number, type, and location of the magnets or magnet bars may be altered in various ways and still achieve saturation, for example, a magnetic flux density of about 1.6 Tesla.

Each of the magnet bars may be attached to a center shaft extending about a central axis of the magnetizer. The magnet bars may extend radially outward from the central shaft, which may have an axis coextensive with the direction of the pipeline. A circumferential magnetizer may create a magnetic field orientation in a direction transverse to the axis of a pipeline. An axial magnetizer may create a magnetic field orientation in a direction corresponding to the axis of a pipeline.

Hall-effect sensors (or other high-sensitivity sensors), may be placed on each magnet bar between the north and south poles. The sensors, or the sensor heads on which the sensors may be affixed, may be coupled to the central shaft. These sensors may monitor the changes in the magnetic field, which may leak from the internal pipe surface. Changes in flux leakage may occur at areas with corrosion or metal loss, geometric deformations, dents, buckles, wrinkles, and different forms of cracking. Software and human analysis can identify damaged areas and determine the extent of damage. For example, the MFL pig and accompanying software and data analysis may identify the length, width, depth, and location of flaws in the pipeline.

In an embodiment, the pig may include a plurality of sensors. In a more detailed embodiment, the plurality of sensors may include at least one Hall sensor. In an alternate embodiment, the plurality of sensors may include at least one ultrasonic or eddy-current sensor. Some embodiments may include one or more Hall-effect sensors and one or more ultrasonic or eddy-current sensors. In an embodiment, one or more sensors may be disposed on a sensor head, which may have a sloping trapezoid, rhomboid, rectangle, or parallelogram shape.

A sensor head may include a suspension system for positioning and biasing the sensor head. In an embodiment, a sensor head may be positioned and biased with one or more conical springs to allow continuous tracking of the internal surface of the pipe. In an embodiment, a plurality of sensors may be disposed on an articulating, radial floating sensor head to continuously track the surface of the pipeline.

In an embodiment, a pig according to the present disclosure may include one or more magnet bar wear pads. A magnet bar wear pad, in an embodiment, may be arranged and designed to facilitate slow counter-clockwise rotation of a magnetizer or pig.

BRIEF DESCRIPTION OF THE DRAWINGS

The foregoing and other features of the present disclosure will become more fully apparent from the following description, taken in conjunction with the accompanying drawings. Understanding that these drawings depict only several embodiments in accordance with the disclosure and are therefore, not to be considered limiting of its scope. The disclosure will be described with additional specificity and detail through use of the accompanying drawings.

In the drawings:

FIG. 10 shows perspective views of two circumferential magnetizers to illustrate the relationship of the magnet bars according to an embodiment of the present disclosure;

FIG. 17 shows front and side views of an exemplary axial magnetizer in accordance with an embodiment of the present disclosure;

DETAILED DESCRIPTION

Figure 1:
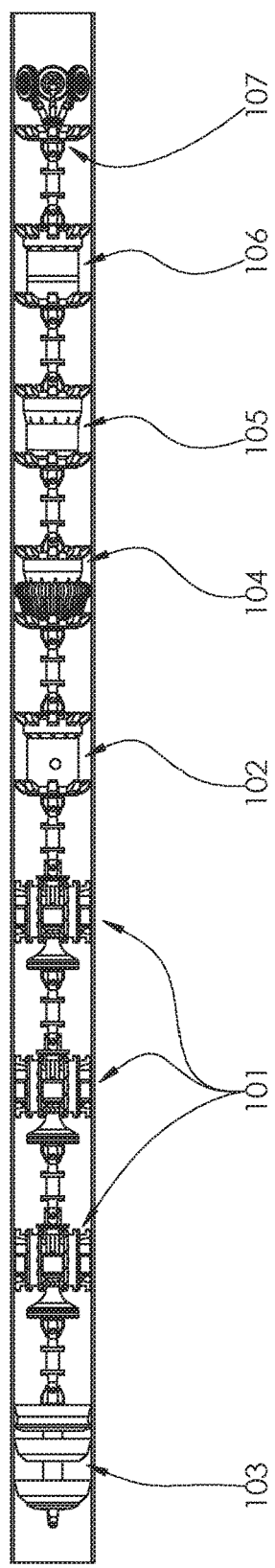
FIG. 1 depicts an MFL pig having a plurality of operatively connected component bodies in accordance with an embodiment of the present disclosure.

In the following detailed description, reference is made to the accompanying drawings, which form a part hereof. In the drawings, similar symbols typically identify similar components, unless context dictates otherwise. The illustrative embodiments described herein are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

This disclosure is generally drawn to apparatus and systems for inspecting pipelines. Examples of this disclosure may be drawn to pigs and pigging systems, smart pigs, MFL pigs, circumferential magnetizers for MFL pigs, and axial magnetizers for MFL pigs. Particular examples may be directed to certain aspects and components of circumferential magnetizers for MFL pigs, including sensor heads, suspension systems for the sensor heads, magnet bar wear pads, and the like. Additional examples may be directed to certain aspects and components of axial magnetizers for MFL pigs, including sensor heads, suspension systems for the sensor heads, magnet bar wear pads, and the like.

Circumferential Magnetizer Embodiment

With reference to FIG. 1, an exemplary embodiment of an MFL pig including circumferential magnetizers is shown. The MFL pig may include several component bodies, including circumferential magnetizers 101, integrated electronic component body 102, and drive section component body 103. Each of circumferential magnetizers 101 may be offset from the other in order to ensure that the entire pipe surface to be inspected is covered by the magnetic circuits and sensors. A geometry module 104 may include mechanical arms for measuring deformations and the internal diameter of the pipeline. An additional module 105 may include an inertial measurement unit for continuous mapping of the pipeline. One or more battery modules 106 may be used to power all systems related to the inspection tool. A rear assembly module 107 may contain a transmitter and odometer. As will be appreciated by one of skill in the art, various other sensors and electronic components may be included on an MFL pig depending on the purpose of the pig and the intended measurements.

Figure 2:
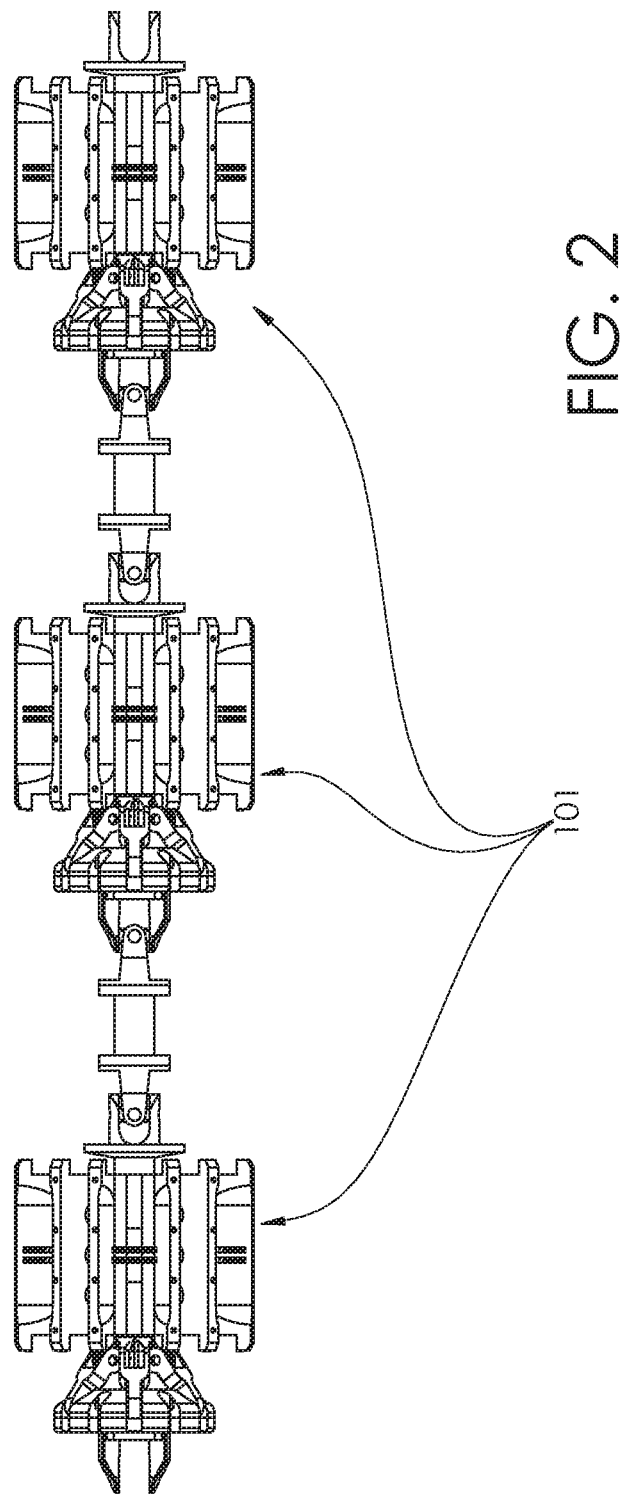
FIG. 2 presents a side view of a portion of an MFL pig having a plurality of operatively connected component bodies in accordance with an embodiment of the present disclosure.

FIG. 2 presents a detailed view of the exemplary embodiment of the MFL pig shown in FIG. 1. The portion of the MFL pig shown in the embodiment of FIG. 2 includes three circumferential magnetizer modules 101. One of skill in the art will appreciate that the component bodies shown need not be in the particular order presented in the figure. The modular structure of the component bodies may also enable easy repair of the pig by allowing a technician to swap out a component body in need of repair, thus allowing the pig to remain in service more continuously.

A circumferential magnetizer 101 in accordance with the present disclosure may include several components, including magnet systems, sensor systems, sensor suspension systems, magnet bar wear pads, and other related components. A circumferential magnetizer in accordance with the present disclosure may include one or more magnets oriented and configured to induce a magnetic field transverse to the axis of the pipeline. In an embodiment, a magnetizer may include a plurality of banks of magnets disposed circumferentially around a central shaft of a magnetizer. In an embodiment, sensors may be disposed between the banks of magnets.

Figure 3:
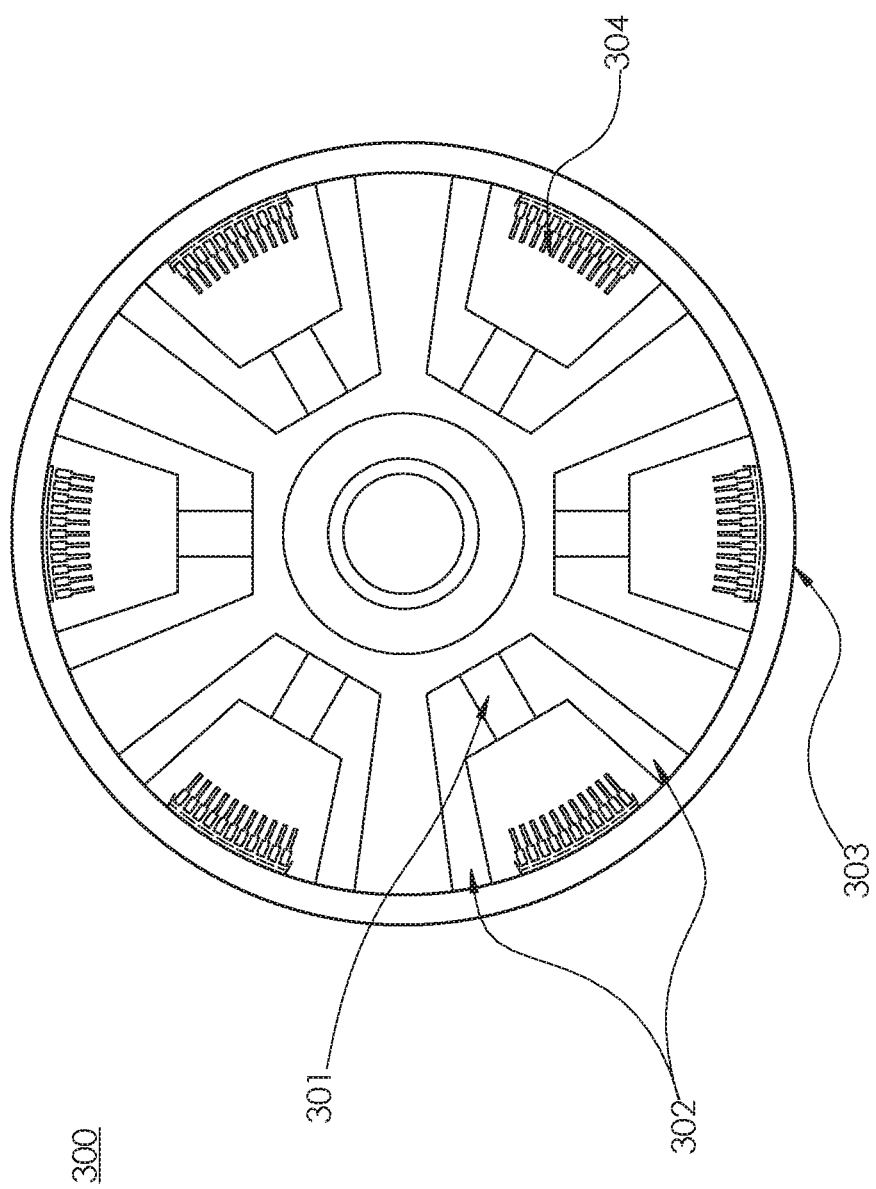
FIG. 3 is a sectional schematic diagram of a circumferential magnetizer.

FIG. 3 presents a sectional schematic diagram of a circumferential magnetizer. Circumferential magnetizer 300 may include magnets 301, magnetic circuit poles 302, and sensors 304. Each magnet 301 and corresponding magnetic circuit poles 302 may form a magnet bar. The position of the sensors 304 relative to the pipe wall and within the magnetic circuit can be seen. FIG. 3 illustrates the location 303 of flux leakage from the pipe wall and its relationship to the sensors. This diagram illustrates the general layout of components of circumferential magnetizer 300 and is not necessarily drawn to scale. As will be appreciated by one of skill in the art, magnetic flux 303 will not be visible, but its position is included for descriptive purposes. Magnets 301 may be disposed at several locations in a circumferential direction about circumferential magnetizer 300. Magnets 301 may include one or more banks of magnets at each location. For example, FIG. 3 illustrates magnets 301 at six circumferential locations; each location may include one or more magnets 301 extending axially, which is not visible from the sectional schematic drawing. Magnetic circuit poles 302 may be provided to impart magnetic flux from magnets 301 to the interior of a pipe and thereby magnetize the pipe wall. Separate wear inserts may be coupled to magnetic circuit poles 302 to extend the wear life of the mag bars. Sensors 304 may be positioned between magnetic circuit poles 302 to monitor the magnetic flux through the pipe wall and detect magnetic flux leakage.

As described above, a circumferential magnetizer may include a plurality of magnets or a plurality of banks of magnets. The magnets, together with the magnetic circuit poles, may form magnet bars. The magnet bars may be spaced evenly apart from each other and may extend radially outward from the central shaft, the central shaft being coaxial with the length of the pipeline. For example, a circumferential magnetizer may include two or more magnet bars, each magnet bar having a pair of magnetic circuit poles with the sensors disposed between the magnetic circuit poles. The sensor head may include a plurality of sensors. The magnet bars may include a plurality of magnets, each magnet being aligned in the same polarity. A magnetic circuit pole may contact one pole of a magnet and extend from the magnet radially outward toward a pipe wall. Another magnetic circuit pole may contact the opposite pole of the magnet and extend from the magnet radially outward toward the pipe wall. A sensor head may be disposed between these magnetic circuit poles. In this manner, a magnetic field may flow between the magnetic circuit poles and across the sensor head disposed between the magnet bars. When the magnetic circuit poles contact the pipe wall, a magnetic circuit may be created, and the sensors on the sensor head may monitor the magnetic flux and detect any magnetic flux leakage from the pipe wall.

In an embodiment, a circumferential magnetizer may include two or more magnet bars, each including one or more magnets. In an embodiment, each magnet bar may include a plurality of magnets, each magnet having the same orientation. Each magnet may include a first side having a first polarity and a second side having a polarity opposite to the first polarity. A first magnetic circuit pole may extend radially outward from the side of a magnet having a first polarity toward the pipe wall, and a second magnetic circuit pole may extend radially outward from the side of a magnet having the opposite polarity toward the pipe wall. Positioning magnets and magnetic circuit poles in this manner allows a magnetizer to impart a magnetic field circumferentially around the interior of a pipeline in an orientation transverse to the axis of the pipeline. This orientation may allow for axially oriented defects, such as a narrow axial metal loss or corrosion, loci of damage, some forms of axial cracking, or longitudinal seam weld defects extending axially down a portion of the pipeline to be detected.

The magnets in a circumferential magnetizer may be permanent magnets or electromagnetic magnets. In an embodiment, the magnets may be rare-earth permanent magnets. In an embodiment, the magnets may be neodymium-based magnets.

Each magnetic circuit pole may include one or more wear pads. A magnetic circuit pole wear pad may protect a magnetic circuit pole from the interior surface of the pipeline or debris within the pipeline interior. This may extend the amount of usable time between repairs. In an embodiment, a magnetic circuit pole wear pad may comprise one or more inserts. In a detailed embodiment, the magnetic circuit pole wear pad may comprise a plurality of carbide or ceramic inserts. In an embodiment, one or more magnetic circuit poles may include one or more carbide or ceramic inserts disposed directly into the magnetic circuit pole(s). Carbide or ceramic inserts may provide beneficial reductions in drag force. Carbide or ceramic inserts may reduce drag force by as much as 30% from conventional designs. Each magnetic circuit pole wear pad, if included, may be maintained at an angle with respect to the axis of the pipeline. A magnet bar wear pad, in an embodiment, may be arranged and designed to facilitate slow counter-clockwise rotation of a magnetizer or pig. Alternatively or in addition, the carbide or ceramic inserts, if included, may be disposed in a pattern designed to facilitate a slow rotation of the pig.

One or more sensor heads may be placed in each magnet bar. The one or more sensor heads may be disposed between magnetic circuit poles and may therefore be positioned to measure magnetic flux through a pipe wall. Each sensor head may include one or more sensors. The magnets may saturate a portion of pipeline to be inspected with a circumferential magnetic field. The sensors may measure the magnetic field and, in particular, may detect changes or aberrations in the magnetic field. Defects in the pipeline, including corroded areas, areas missing metal, geometric deformations, dents, buckles, wrinkles, cracks, and the like may induce aberrations and changes into the magnetic field, or the magnetic field may leak at the particular location of a defect.

Figure 4:
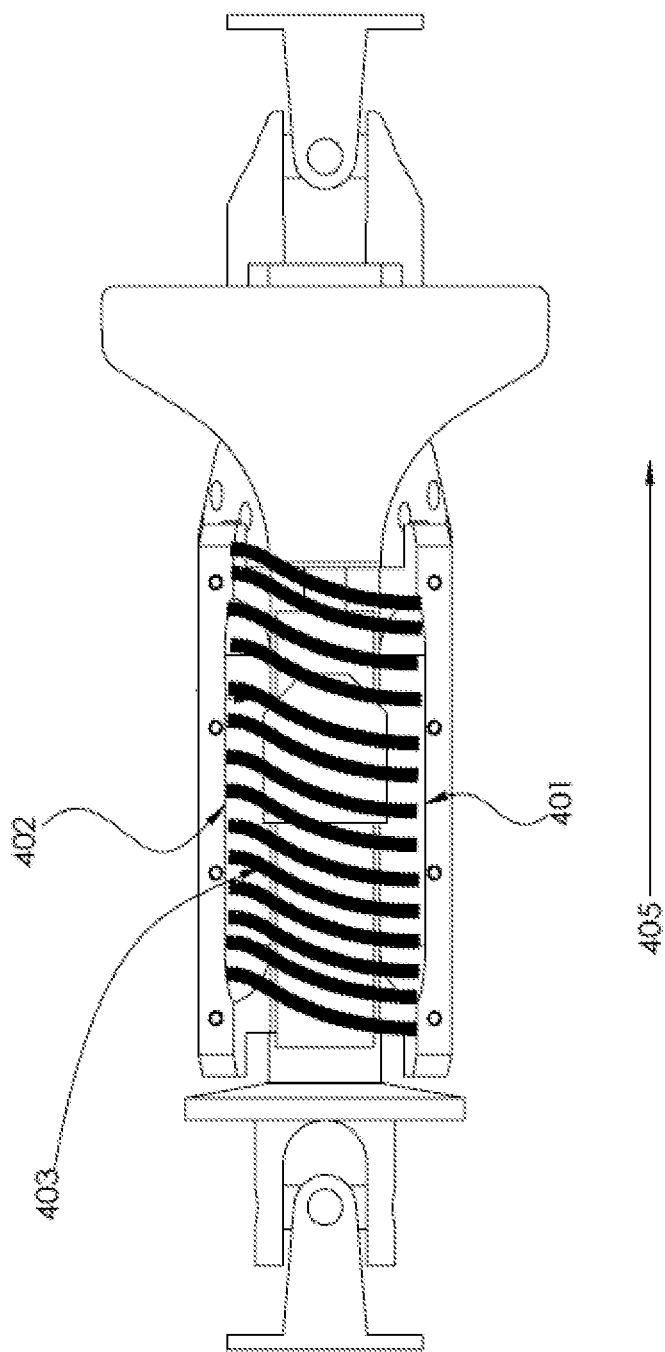
FIG. 4 depicts a schematic diagram of a magnet bar and shows the direction of the magnetic field in relation to the sensors and a crack-like defect, in accordance with an embodiment of the present disclosure.

For example, FIG. 4 depicts a single magnet bar. Each magnet bar may include magnets having a first polarity 401 (e.g., a south pole) and a second polarity 402 (e.g., a north pole) opposite to the first polarity 401. Note that the nomenclature and particular polarity assigned for the purposes of the written description is largely arbitrary; for example, north could be called positive, and south could be called negative. A south magnetic circuit pole 401 may couple the south pole side of the magnets to the pipe wall, and a north magnetic circuit pole 402 may couple the north pole side of the magnets to the pipe wall. Further, it is important that a sensor head be flanked on either side by magnetic circuit poles of opposing polarities to establish a magnetic field extending over and through the sensor head and sensors; this will be explained in further detail later The circumferential magnetizers may travel through a pipe having an internal diameter less than the nominal diameter of the magnetizer and may be configured to closely articulate with the pipe wall. A pipe may have some structural aberration, such as a crack or crack-like anomaly. The magnetic field from the magnets may be imparted to the pipe wall by south magnetic circuit pole 401 and north magnetic circuit pole 402. For visualization and descriptive purposes, magnetic flux lines 403 are superimposed onto the diagram. Sensors may be placed between magnets to be within the magnetic field. The magnetic field may be disrupted when the circumferential magnetizer passes over an aberration, and the disruption in the magnetic field may be detected by the sensors. Arrow 405 represents a direction of travel through a pipe.

Figure 5:
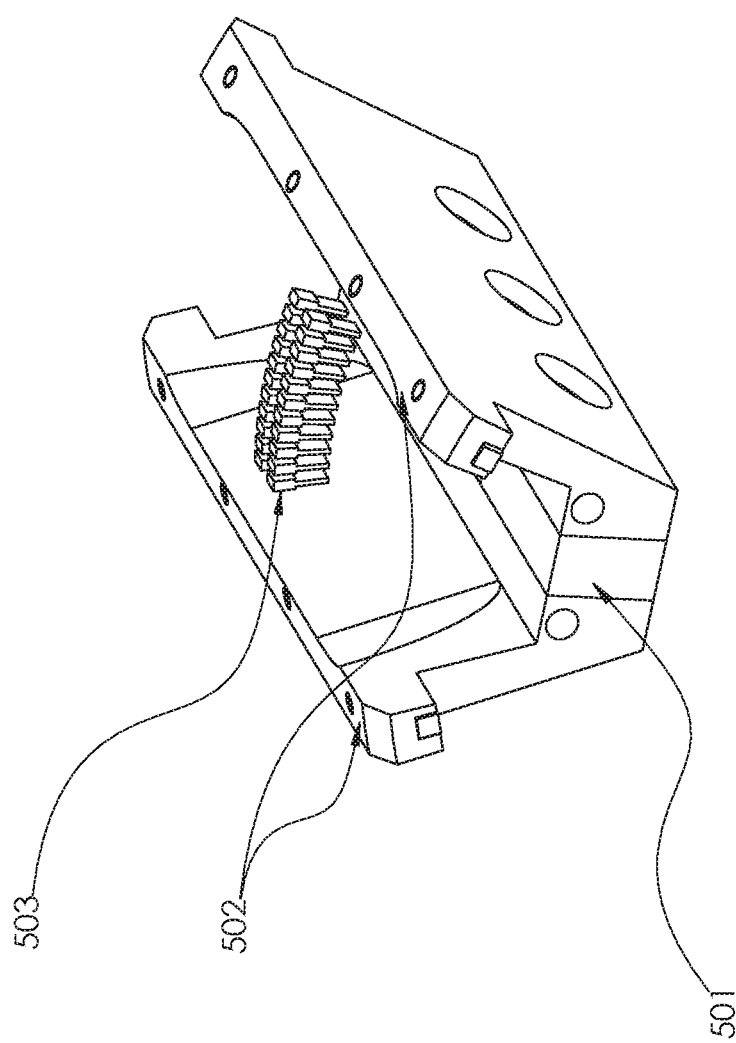
FIG. 5 presents an illustration of sensor placement relative to magnet and magnet bar placement on a circumferential magnetizer in accordance with an embodiment of the present disclosure.

In an embodiment, a magnet bar may include a plurality of sensors between each magnetic circuit pole to measure the magnetic flux imparted into the pipe. FIG. 5 generally illustrates the placement of sensors relative to the magnets. FIG. 5 shows a circumferential magnetizer having magnets 501, magnetic circuit poles 502, and sensors 503. Sensors 503 may be positioned between magnetic circuit poles 502. Magnetic circuit poles 502 may impart a magnetic flux into a pipe wall, and the magnetic flux may flow from one magnetic circuit pole to the other. Sensors 503 positioned within the magnetic field may take measurements of the magnetic flux. In an embodiment, sensors 503 may take measurements of the magnetic flux as closely as every 0.039" (1 mm) in the axial direction of the pipe. In an embodiment, sensors 503 may take measurements of the magnetic flux as closely as every 0.050" (1.25 mm) in the axial direction of the pipe. In an embodiment, sensors 503 may comprise Hall-effect sensors. In an embodiment, a circumferential magnetizer may include six magnet bars and may have 72 Hall sensors per diameter-inch. Aberrations in the pipe may cause distortions or disruptions in the magnetic field, and the sensors may thus detect the irregularities in the magnetic field corresponding to the aberration in the pipe. A magnetizer utilizing a circumferentially oriented magnetic field may be particularly adept at detecting axially oriented flaws and inspecting longitudinal welds of a pipeline. A magnetizer utilizing a circumferentially oriented magnetic field may be able to detect flaws of 0.8 inches (20 mm) with an opening of 0.004" (0.1 mm). A sensor head may be able to survive forces of up to about 20G, and sensors may be able to withstand pressures of up to 2,000 psi (13.8 Mpa) and velocities of up to 30 ft/s (9 m/s).

In an embodiment, each sensor head may include a plurality of sensors 503. The plurality of sensors 503 may include Hall-effect sensors, eddy-current sensors, ultrasonic sensors (such as EMAT sensors), or combinations thereof. The responses of each sensor may be combined and analyzed to locate or define certain pipeline defects, as discussed above. For example, a Hall-effect sensor may detect a response to a magnetic field leakage. The output of a Hall-effect sensor may vary linearly or nonlinearly with respect to changes in the magnetic field. These changes may reflect the presence of a flaw, defect, or anomaly. The output of a plurality of such sensors, in the aggregate, may allow for an ultra-high resolution sampling in a given area of the internal pipe surface, thereby allowing defects to be accurately detected, characterized, analyzed, and quantified. In an embodiment, a circumferential magnetizer according to an aspect of the present disclosure may measure and store flux leakage values to a sampling density of up to 500 per square inch (80 square cm). In an embodiment, a circumferential magnetizer according to the present disclosure may include several sensor heads, each sensor head having a plurality of individual sensors. In an embodiment, a pig may include three circumferential magnetizer modules with six sensor heads per module and 24 Hall-effect sensors per sensor head. This exemplary embodiment would yield a total of 432 Hall-effect sensors on the circumferential magnetizer. In an exemplary embodiment, a smart pig may have a diameter greater than six inches and contain three circumferential magnetizer modules, wherein each module includes six sensor heads and each sensor head includes 24 Hall-effect sensors. Such a circumferential magnetizer could be said to have a sensor density of 72 sensors per diameter-inch.

In an embodiment, a circumferential magnetizer may have a sensor density of between about 60 to 100 sensors per diameter-inch.

A circumferential magnetizer may be sized to have a nominal diameter slightly larger than the diameter of a pipe. For example, a circumferential magnetizer slightly larger than six inches in diameter may be configured to travel through a six-inch pipe. One of skill in the art will recognize that a circumferential magnetizer according to the present disclosure may be sized to inspect pipes of alternate diameters.

Figure 6:
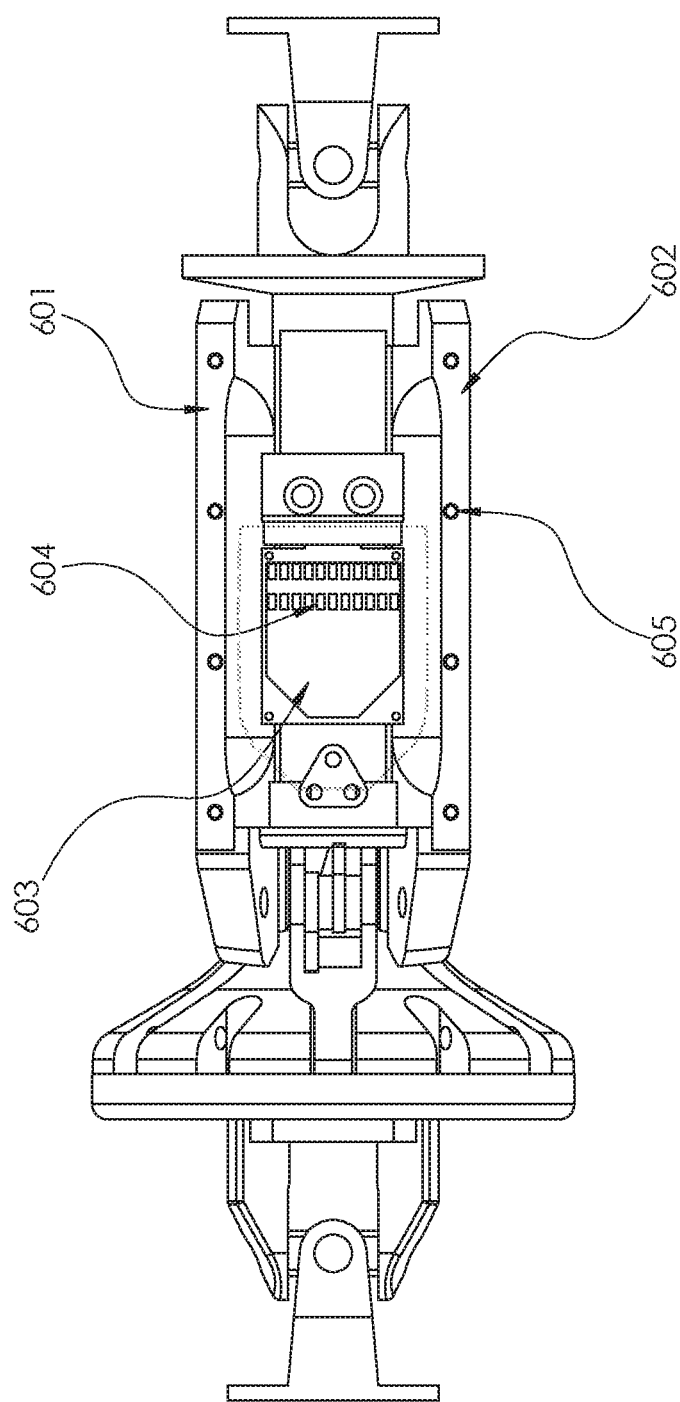
FIG. 6 shows a top view of a circumferential magnet bar in accordance with an embodiment of the present disclosure.

FIG. 6 shows a top view of a magnet bar of a circumferential magnetizer in accordance with an embodiment of the present disclosure. In the embodiment shown in FIG. 6, a circumferential magnetizer may include a north magnetic circuit pole 601 extending from a north-polarity side of one or more magnets and a south magnetic circuit pole 602 extending from a south-polarity side of one or more magnets. When north magnetic circuit pole 601 and south magnetic circuit pole 602 contact a pipe wall, a magnetic flux may extend between magnetic circuit poles 601, 602. Sensor head 603 may be disposed between magnetic circuit poles 601, 602. Sensor head 603 may include one or more sensors 604. In an embodiment, sensors 604 may be Hall-effect sensors. In an embodiment, there may be 24 sensors 604 disposed on sensor head 603. In an embodiment, the magnet bar of FIG. 6 may include one or more magnets. In an embodiment, the magnet bar of FIG. 6 may include three magnets.

Magnetic circuit poles 601, 602 may contact the interior of the pipeline. In an embodiment, magnetic circuit poles 601, 602 may function as a flux coupler to more efficiently saturate a pipe wall with a magnetic field. In a detailed embodiment, magnetic circuit poles 601, 602 may include wear pads 605 on at least a portion of a surface that contacts the pipe wall. Wear pads 605 may comprise one or more ceramic or carbide inserts, as depicted in FIG. 6. Ceramic or carbide inserts may protect the magnetic circuit poles from wear and may reduce drag force. In an embodiment, ceramic or carbide inserts may reduce drag force by about 30%.

Figure 7:
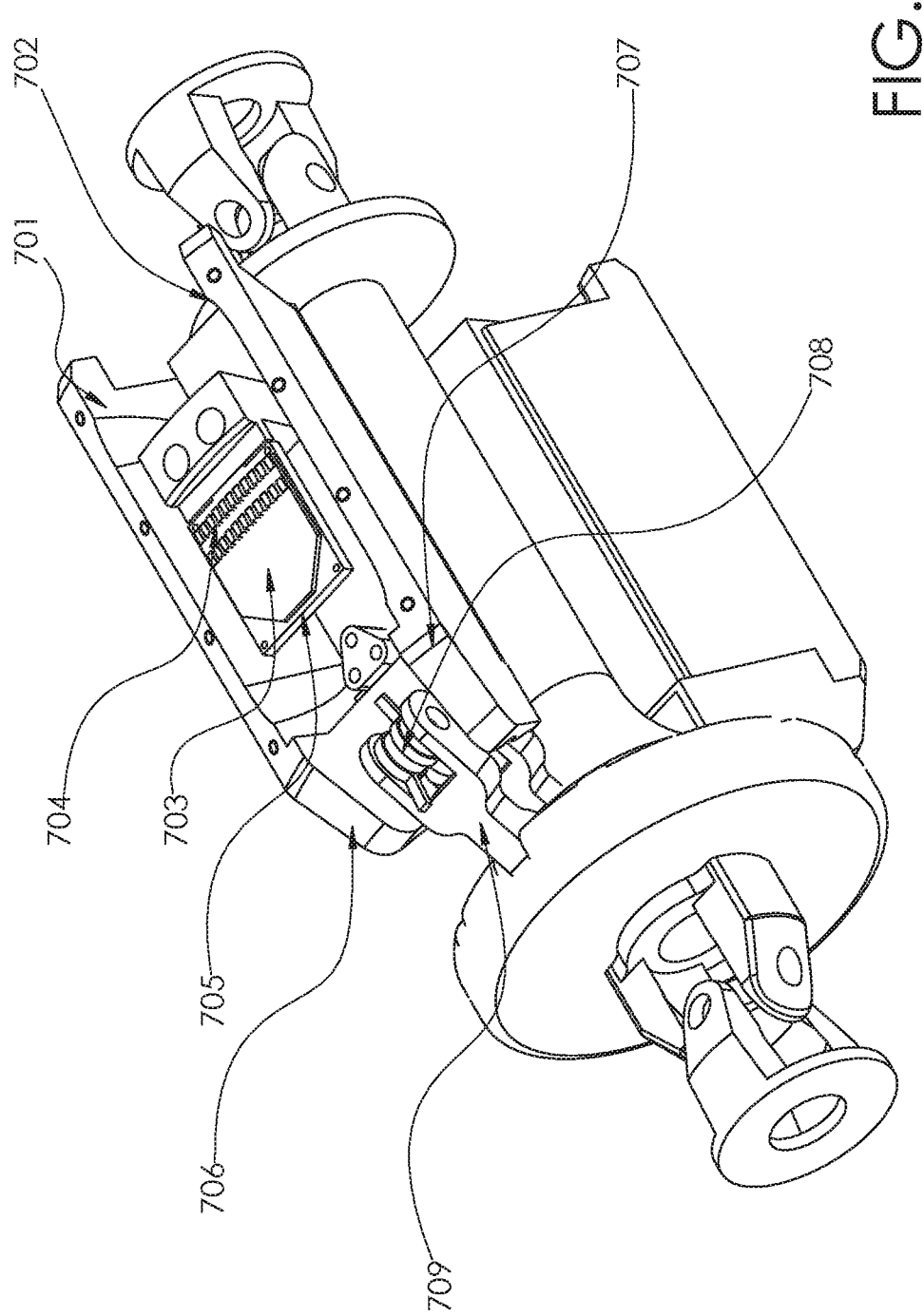
FIG. 7 depicts a perspective view of a circumferential magnetizer in accordance with an embodiment of the present disclosure.

FIG. 7 depicts a perspective view of a circumferential magnetizer in accordance with an embodiment of the present disclosure. In the embodiment shown in FIG. 7, a circumferential magnetizer may include north magnetic circuit pole 701 extending from a north-polarity side of one or more magnets, south magnetic circuit pole 702 extending from a south-polarity side of one or more magnets, sensor head 703, and a plurality of sensors 704 disposed on sensor head 703. In an embodiment, sensors 704 may be Hall-effect sensors, and there may be 24 sensors 704 disposed on sensor head 703. A sensor head wear pad 705 may be coupled to sensor head 703. Sensor head wear pad 705 may articulate with the pipe and may function to protect sensors 704.

Sensor head wear pad 705 may comprise a nickel-based alloy or superalloy. Magnetic circuit poles 701, 702 may include a ceramic insert or coating. In detailed embodiments, the ceramic may comprise silicon carbide. In alternate detailed embodiments, the inserts may comprise tungsten carbide.

The circumferential magnetizer according to the embodiment depicted in FIG. 7 may include a means for collapsing 706 magnetic circuit poles 701, 702. Means for collapsing 706 may comprise front links 707, upper link 709, and torsion spring 708. Means for collapsing 706 may exert a sufficient force, such as a spring force, to maintain the magnetic circuit poles 701, 702 in engagement with the pipe wall but may collapse, entirely or partially, if the magnetic circuit poles 701, 702 encounter an aberration in the pipe, such as an indentation, or if the pig including the circumferential magnetizer encounters a bend in the pipe. In an embodiment, sensor head 703 is also operatively coupled to the means for collapsing 706. In an alternate embodiment, sensor head 703 includes an independent sensor head suspension system. Sensor head suspension system may include one or more conical springs coupling the bottom of the sensor head 703 to the central shaft. In an embodiment, sensor head suspension system comprises dual conical springs. Both means for collapsing 706 and sensor head suspension system may enable components of the circumferential magnetizer to collapse up to 25% of the outside diameter of the pipe; that is, the diameter of at least part of the circumferential magnetizer may be reduced by up to 25% when encountering an aberration in the pipe or when going around a bend in the pipeline. These features may allow a pig to navigate pipeline bends of greater than or equal to 1.5D (where D is equal to the pipe diameter). In an embodiment, these features may allow a pig to navigate pair of 1.5D bends separated by a pipeline distance equal to 3D. The collapsibility features may reduce drag force on the circumferential magnetizer, which may help to prevent a pig from stalling when navigating a relatively tight bend.

Figure 8:
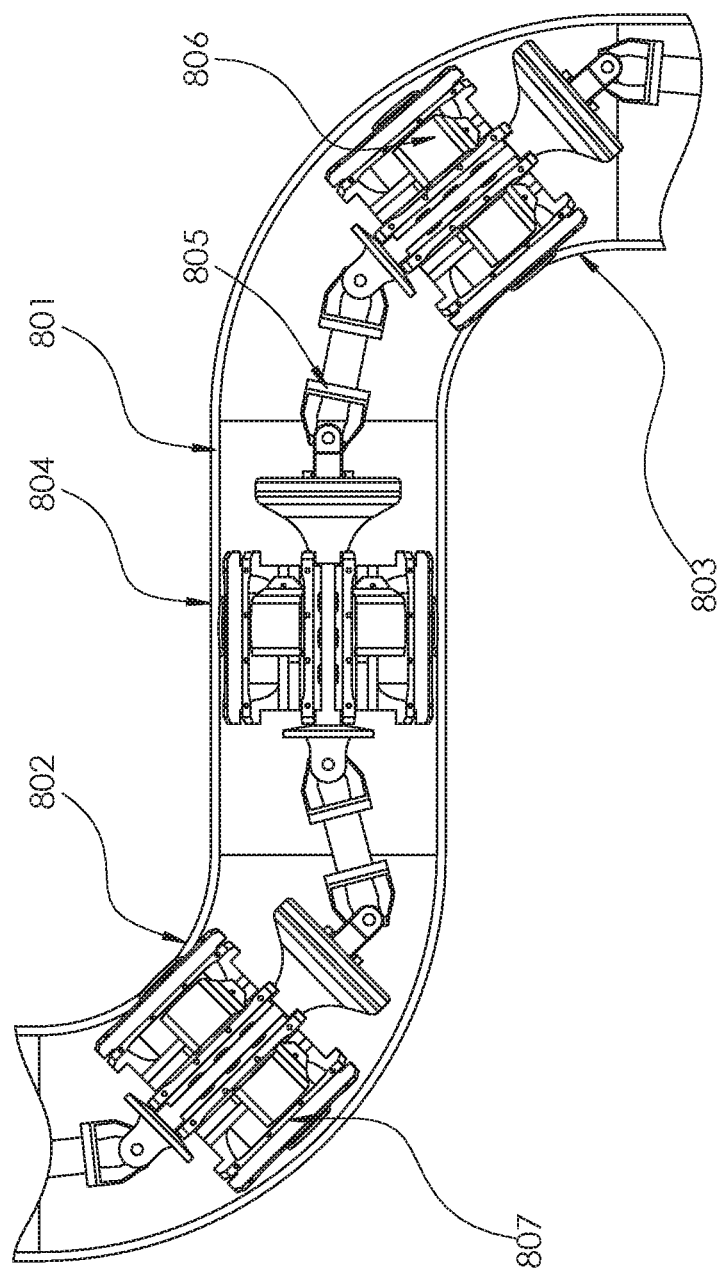
FIG. 8 shows a plurality of circumferential magnetizers according to an embodiment of the present disclosure operatively linked together and navigating bends in a pipeline.

FIG. 8 shows a plurality of circumferential magnetizers according to an embodiment of the present disclosure operatively linked together navigating bends in a pipeline. A plurality of circumferential magnetizers 804 may be operatively linked together by linking means 805. Linking means 805 may be able to rotate about the center shaft and may include features allowing for some transverse rotation about a bolt incorporated in the linking means. These features of linking means 805 can be seen with reference to FIG. 8. Each circumferential magnetizer 804 may include a plurality of magnet bars 807. Each magnet bar 807 may include magnetic circuit poles and one or more sensor head(s) 806 including a plurality of sensors. A pig including circumferential magnetizers 804 may be capable of navigating complex bends in a pipeline 801. For example, each bend 802, 803 may have a bend configuration of greater than or equal to about 1.5D. In an embodiment, each bend 802, 803 may have a bend configuration with a pair of 1.5D bends separated from each other by a pipeline distance equal to 3D. Circumferential magnetizers 804 may have a diameter of about six inches. If pipeline 801 has a nominal diameter of six inches, there may be a distance of about 18 inches between the bends 802, 803. Generally speaking, circumferential magnetizers 804 according to at least one embodiment of the present disclosure may be capable of navigating two bends 802, 803, where one magnetizer 804 simultaneously navigates each bend, if each bend is separated by a distance of about three times the nominal diameter of the pipe. A number of features may contribute to the ability of a pig including three circumferential magnetizers to navigate such complex bends without stalling, including but not limited to the means for collapsing the magnet bar, which provides the circumferential magnetizers with a collapsibility of about 25%; the length of the magnet bars and the center shaft; and the design of the universal joints, which provide connections among the various modules comprising the smart pig. These features may be seen with reference to FIG. 8.

A smart pig may be propelled through a pipe while product is moving through the pipe. The moving product may exert a pressure on an aft end of a smart pig, or on the aft end of one or more modules comprising a smart pig, which may propel the pig through the pipe. The speed at which a pig and its constituent modules travels is accordingly a result of the differential pressure at an aft end of the pig compared to the forward end of the pig. To take consistent measurements, it is desirable to maintain the differential pressure as close to constant as possible to keep the speed of the pig as close to constant as possible. When encountering a bend in a pipeline, conventional pigs tend to experience increased drag force that slows down and often stalls the pig in the pipeline. When a pig stalls, the differential pressure at the aft end of the pig builds until the pig is shot free. However, a pig that is shot in such a manner may be travelling too fast to take reliable measurements. This speed may also increase the risk of damage. The means for collapsing and the carbide wear inserts coupled to the magnetic circuit poles of circumferential magnetizer of the present disclosure may help to reduce the drag force experienced in a bend, allowing the circumferential magnetizer modules to maintain a constant speed through a bend, which may further enable more accurate measurements to be taken throughout the pipeline, particularly in areas right after a bend. In an embodiment, a smart pig including three circumferential magnetizers may be able to navigate a pair of 1.5D bends separated from each other by a pipeline distance equal to 3D.

Figure 9:
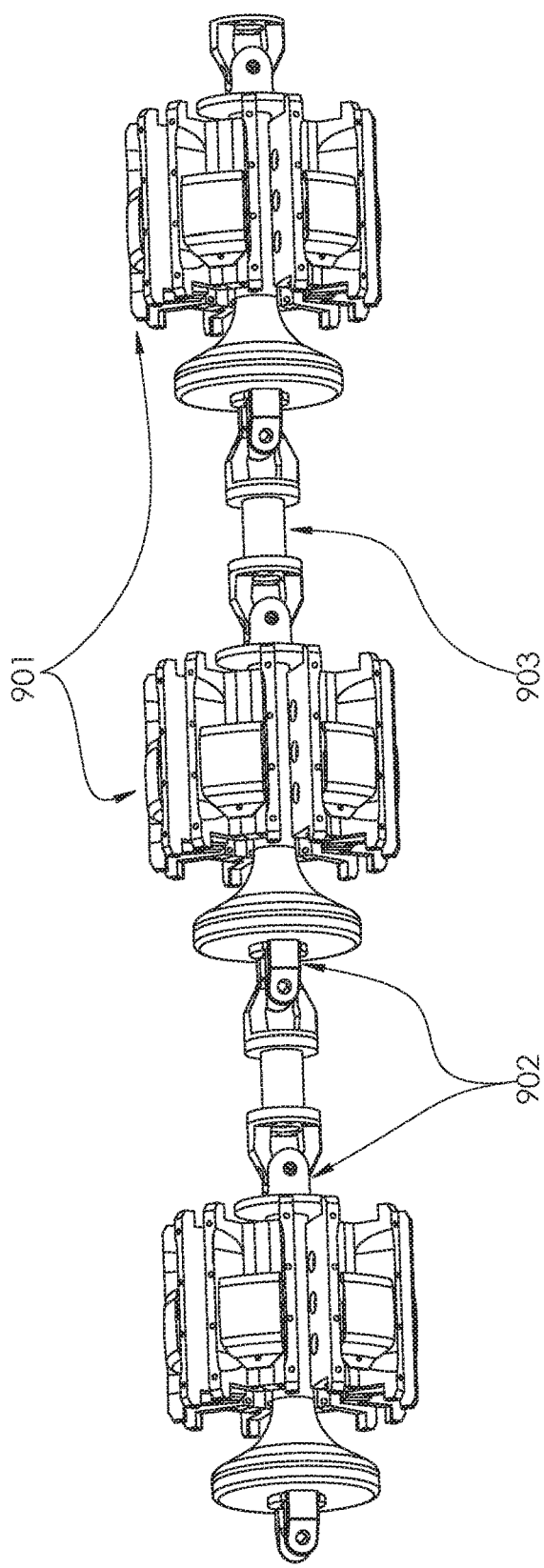
FIG. 9 shows a plurality of circumferential magnetizers and their mechanical relationship to each other according to an embodiment of the present disclosure.

FIG. 9 depicts the three circumferential magnetizers 901. Circumferential magnetizers 901 may be connected to each other with universal joints 903, which are connected to the central shaft by linkage components 902. The universal joints may be angle controlled. The circumferential magnetizers 901 may be oriented relative to each other to ensure complete, 360-degree coverage of the inside of a pipe. Universal joints 903 may maintain the orientations of the circumferential magnetizers with respect to each other. The central shaft, linkage components 902, and universal joints 903 may comprise titanium to maintain strength, provide corrosion resistance, and reduce weight. In an embodiment, the central shaft, linkage components 902, and universal joints 903 may be comprised entirely of titanium.

FIG. 10 includes a front view 1001 and an isometric view 1002 of a circumferential magnetizer module according to an embodiment of the present disclosure. FIG. 10 shows that each module may have six magnet bars, each with a magnet 1003. Each magnet bar may provide approximately 20 degrees of pipe wall coverage. Three such modules may allow a pig to provide 360-degree coverage. Providing a smart pig with three modules may, for example, allow complete coverage in a six-inch pipe, but other tool diameters may require a different number of bars or modules.

Figure 11:
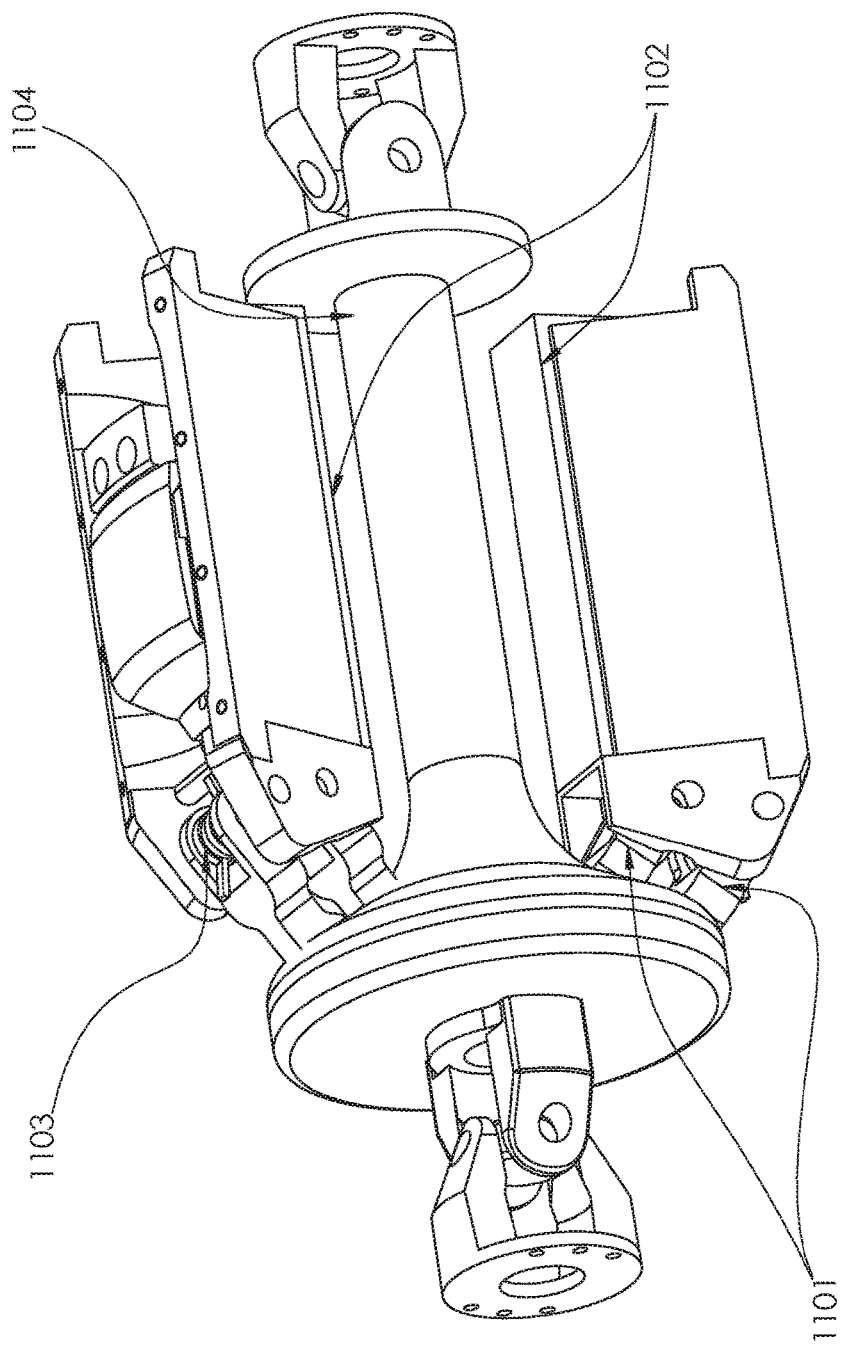
FIG. 11 shows the suspension system of the magnet bars and illustrates the ability of the magnet bars to track the pipe surface according to an embodiment of the present disclosure.

FIG. 11 provides a side view of a circumferential magnetizer module showing just two bars and their respective means for collapsing. Means for collapsing includes upper and lower parallel links 1101, which join the magnet bars to the central shaft 1104. The parallel links ensure that the magnet bars 1102 continually remain in good contact and parallel to the pipe surface and central shaft 1104. The torsion springs 1103 mounted on the upper link of each magnet bar keep the module centered and allow the magnet bars to collapse toward central shaft 1104 when passing over obstacles or negotiating bends and other bore restrictions.

Figure 14:
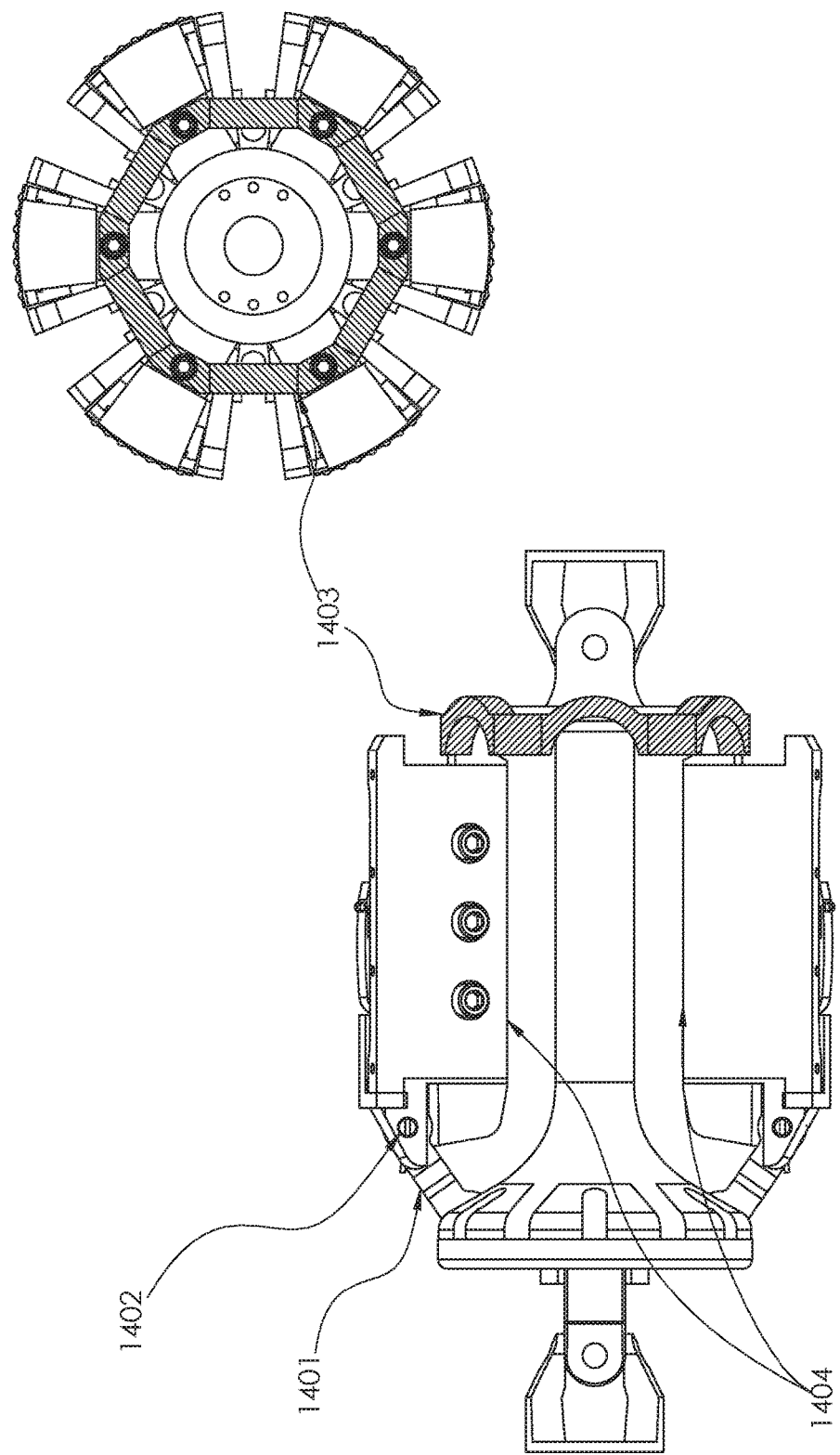
FIG. 14 shows a side view of an embodiment of a circumferential magnetizer with a magnet bar removed to illustrate certain features.

In an embodiment, each magnet bar may include rear links similar to links 1101 to join the rear end of each magnet bar to the central shaft 1104, along with a torsion spring. Such an embodiment may maintain the entire magnet bar in contact with the pipe wall. Alternatively, as shown in FIG. 14, each magnet bar 1404 of a circumferential magnetizer may include a front control link 1401 and a torsion spring 1402. Torsion spring 1402 may support the weight of each magnet bar and may help to support the weight of the central shaft. The rear portion of a circumferential magnetizer may include a polyurethane ring 1403. Polyurethane ring 1403 may help to maintain each magnet bar biased against the pipe wall but may also help to balance forces, especially when encountering aberrations in the pipeline or when navigating bends. Polyurethane ring 1403 may include bends, which may allow polyurethane ring 1403 to temporarily collapse and allow the magnet bar(s) 1404 to collapse toward the center shaft. Ring 1403 may be made from polyurethane for durability and chemical resistance concerns; however, one of skill in the art may recognize alternative materials from which ring 1403 may be constructed, such as silicone or a durable, chemical-resistant thermoplastic.

Figure 12:
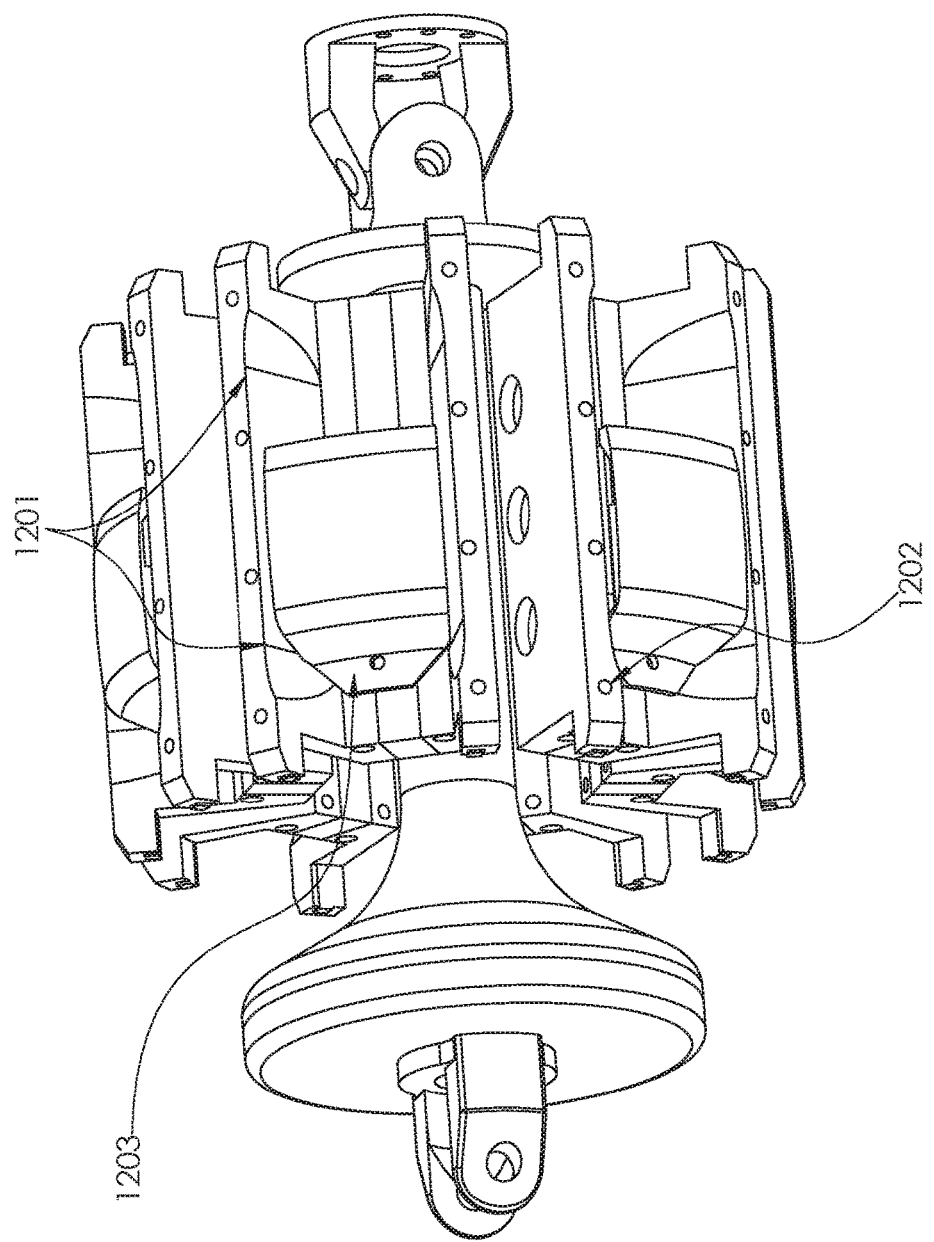
FIG. 12 presents a side perspective view of a circumferential magnetizer according to an embodiment of the present disclosure.

FIG. 12 illustrates a side view of circumferential magnetizer module. The circumferential magnetizer according to the embodiment of FIG. 12 includes magnetic circuit poles 1201. Magnetic circuit poles 1201 may be curved and thickened at their forward and aft ends. Magnetic circuit poles 1201 may include wear pads 1202. The curvature and end thickening, which is visible in FIG. 12, may help to concentrate the magnetic flux and create greater magnetic uniformity across sensor head 1203. Sensor head 1203 may include a wear plate and may include a single attachment point. The single attachment point may facilitate both radial movement and internal surface curvature tracking.

Figure 13:
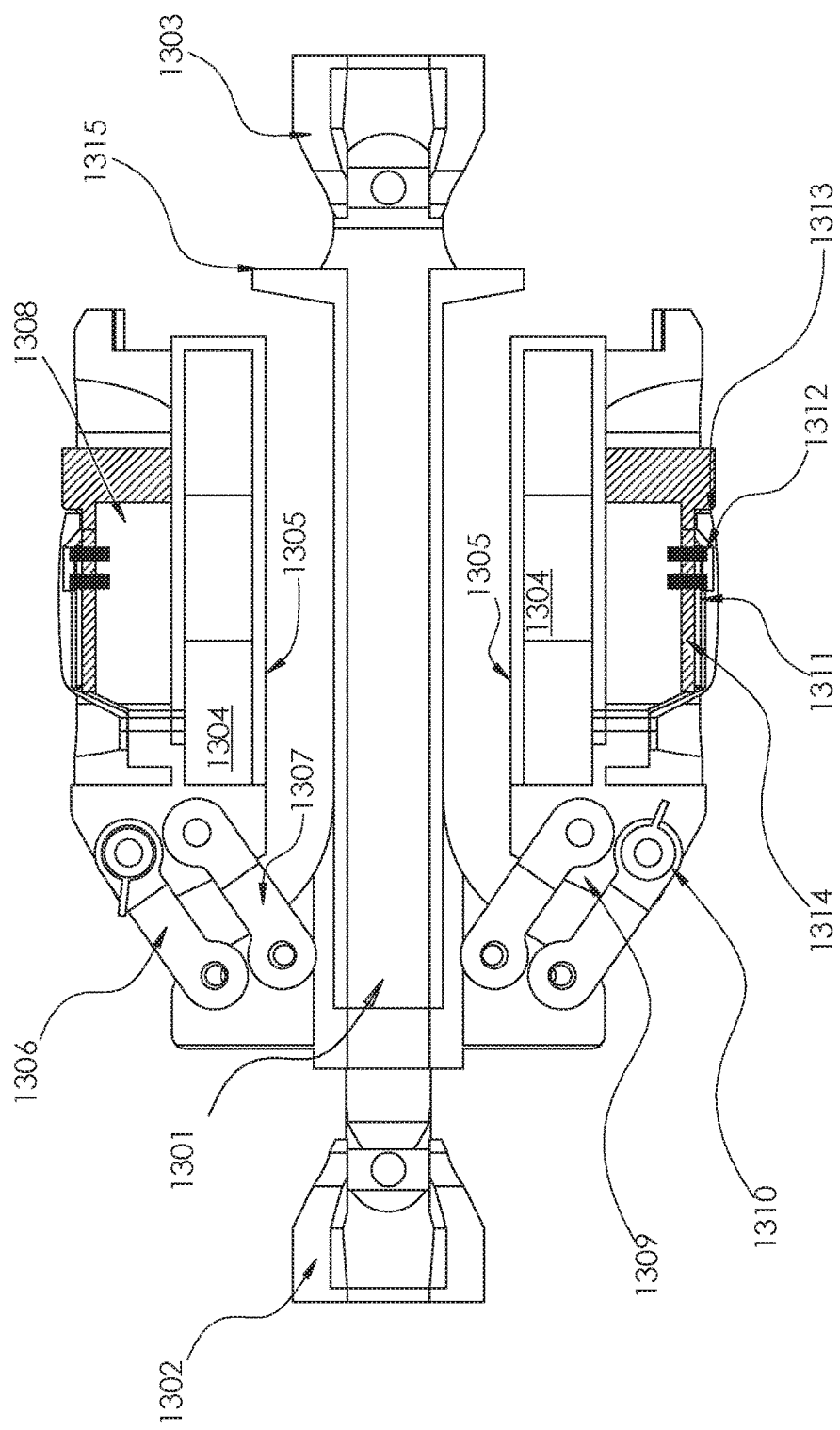
FIG. 13 shows a cross sectional view of one of the magnetizer modules showing key components of the design, according to an embodiment of the present disclosure.

FIG. 13 provides a sectional view of a circumferential magnetizer module according to an embodiment of the present disclosure. The circumferential magnetizer module may include a hollow central shaft 1301, front universal joint 1302, rear universal joint 1303, magnets 1304, magnet shields 1305, and upper and lower magnet bar to center shaft attachment links 1306, 1307. A circumferential magnetizer module may include a sensor head base plate 1314, a sensor head 1311, a plurality of sensors 1312 disposed on sensor head 1311, a wear pad 1313, and conical springs 1308 for suspension of the sensor head 1311. FIG. 13 also illustrates the location of torsion spring 1310. Central shaft 1301 may extend to universal joint limiter 1315, which limits the movement of the universal joints 1303 and keeps the magnetizers in proper orientation with respect to one another to maintain 360-degree pipe wall coverage.

A sensor head 1311 may be in the shape of a sloping trapezoid. The approach angle of a sensor head according to such a design may minimize the transmission of mechanical shocks and vibrations to the sensors and electronics. Furthermore, such a sensor head design may provide a longer wear life, which may contribute to a longer inspection time of a smart pig between repairs. In an embodiment, one or more sensor heads 1311 may extend radially outward and articulate with a surface of a pipeline to track the pipeline surface. In an alternate embodiment, sensor head 1311 may be shaped as a parallelogram or a rhomboid.

Figure 15:
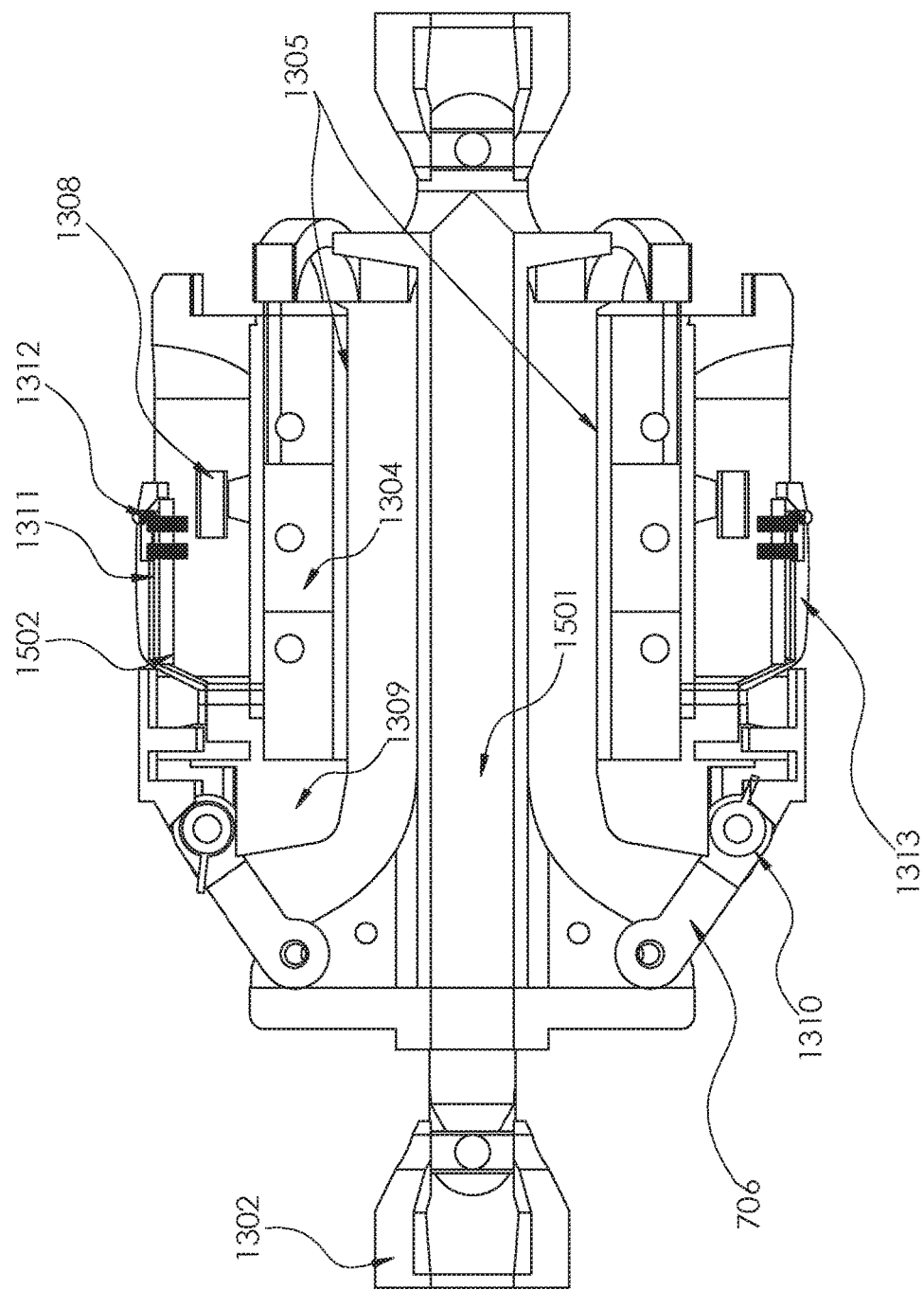
FIG. 15 shows a cross-section of a side view of a circumferential magnetizer in accordance with an embodiment of the present disclosure.

FIG. 15 presents a cross-sectional side view of an embodiment of a circumferential magnetizer including features already described herein. A plurality of magnet bars 1309 are attached to a central shaft 1501 through a means for collapsing 706. The means for collapsing may comprise a torsion spring 1310. Each magnet bar may include a sensor head 1311, a plurality of sensors 1312 disposed on sensor head 1311, a wear pad 1313, a sensor head base plate 1502, magnets 1304, magnet shields 1305, and conical springs 1308 for suspension of the sensor head 1311.

Axial Magnetizer Embodiment

An MFL pig, in addition to or as an alternative to one or more circumferential magnetizers, may include one or more axial magnetizers. An axial magnetizer in accordance with the present disclosure may include several components, including magnet systems, sensor systems, sensor suspension systems, magnet bar wear pads, and other related components. An axial magnetizer in accordance with the present disclosure may include one or more magnets oriented and configured to induce a magnetic field coaxially with the axis of the pipeline. In an embodiment, an axial magnetizer may include a plurality of magnets of a first polarity disposed circumferentially around a front end of a central shaft as well as a plurality of magnets of the opposite polarity disposed circumferentially around a rear end of the central shaft. In an embodiment, sensors may be disposed between the magnets having opposite polarities.

Figure 16:
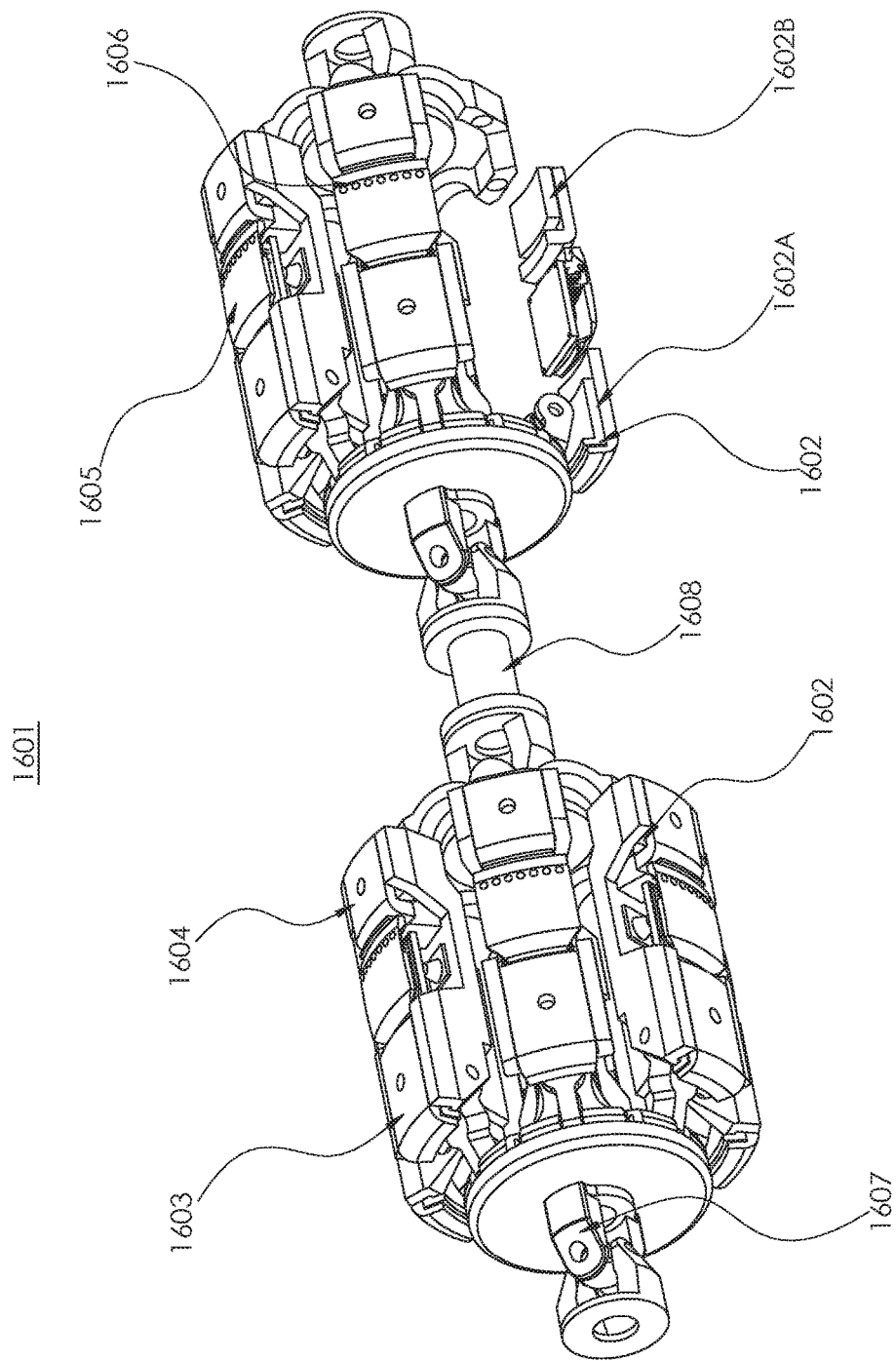
FIG. 16 shows exemplary axial magnetizer modules coupled together in accordance with an embodiment of the present disclosure.

With reference to FIG. 16, which shows two axial magnetizers 1601 coupled together, an axial magnetizer may include a plurality of magnets 1602, which may be coupled to the pipe wall with magnetic circuit poles 1603, 1604. The magnets 1602, together with the magnetic circuit poles 1603, 1604, may form magnet bars. The magnet bars may be spaced evenly apart from each other and may extend radially outward from the central shaft, the central shaft being coaxial with the length of the pipeline. For example, an axial magnetizer may include two or more magnet bars. In an embodiment, an axial magnetizer may include six magnet bars. Each magnet bar may have a pair of magnetic circuit poles 1603, 1604 with sensors 1606 disposed between the magnetic circuit poles 1603, 1604. A sensor head 1605 may include a plurality of sensors 1606. Each magnet bar may include a magnet 1602A disposed toward the front end of the magnet bar having a first polarity and a magnet 1602B disposed toward the rear end of the magnet bar having the opposite polarity. A front magnetic circuit pole 1603 may contact the first pole of the front magnet 1602A and extend from the magnet 1602A radially outward toward a pipe wall. A rear magnetic circuit pole 1604 may contact the opposite pole (i.e., the opposite pole of the front magnet) of the rear magnet 1602B and extend from the magnet 1602B radially outward toward the pipe wall. A sensor head 1605 may be disposed between these magnetic circuit poles. In this manner, a magnetic field may flow between the magnetic circuit poles and across the sensor head 1605 disposed between the magnet bars. When the magnetic circuit poles contact the pipe wall, a magnetic circuit may be created, and the sensors 1606 on the sensor head 1605 may monitor the magnetic flux and detect any magnetic flux leakage from the pipe wall. Positioning magnets 1602 and magnetic circuit poles 1603, 1604 in this manner allows a magnetizer to impart a magnetic field in an axial direction with respect to the axis of the pipeline. This orientation may allow for circumferentially oriented defects, such as a metal loss or corrosion at girth welds, loci of damage, some forms of circumferential cracking, or other defects extending circumferentially around a portion of the pipeline to be detected.

The magnets 1602 in an axial magnetizer may be permanent magnets or electromagnetic magnets. In an embodiment, the magnets may be rare-earth permanent magnets. In an embodiment, the magnets may be neodymium-based magnets.

Axial magnetizers may be connected to each other with universal joints, which connected to the central shaft by linkage components 1607. The universal joints 1608 may be angle controlled. The axial magnetizers may be oriented relative to each other to ensure complete coverage of the inside of a pipe. Universal joints 1608 may maintain the orientations of the circumferential magnetizers with respect to each other. The central shaft, linkage components 1607 and universal joints may comprise titanium to maintain strength, provide corrosion resistance, and reduce weight. In an embodiment, the central shaft, linkage components 1607, and universal joints 1608 may be comprised entirely of titanium.

With reference to FIG. 17, each axial magnetizer may include six magnet bars 1701. Each magnet bar may be designed to cover about 30 degrees of the pipe circumference, such that when each axial magnetizer has six magnet bars, coupling two axial magnetizers to each other may cover about 360 degrees of the pipe circumference. Each magnetic circuit pole may include one or more wear pads 1702. A magnetic circuit pole wear pad 1702 may protect a magnetic circuit pole from the interior surface of the pipeline or debris within the pipeline interior. This may extend the amount of usable time between repairs. In an embodiment, a magnetic circuit pole wear pad 1702 may comprise one or more inserts 1703. In a detailed embodiment, the magnetic circuit pole wear pad 1702 may comprise a plurality of carbide or ceramic inserts 1703. In an embodiment, one or more magnetic circuit poles may include one or more carbide or ceramic inserts 1703 disposed directly into the magnetic circuit pole(s). Carbide or ceramic inserts 1703 may provide beneficial reductions in drag force. Carbide or ceramic inserts 1703 may reduce drag force by as much as 30% from conventional designs. Each magnetic circuit pole wear pad 1702, if included, may be maintained at an angle with respect to the axis of the pipeline. A magnet bar wear pad, in an embodiment, may be arranged and designed to facilitate slow counter-clockwise rotation of a magnetizer or pig. Alternatively or in addition, the carbide or ceramic inserts 1703, if included, may be disposed in a pattern designed to facilitate a slow rotation of the pig.

One or more sensor heads may be placed in each magnet bar. The one or more sensor heads may be disposed between magnetic circuit poles and may therefore be positioned to measure magnetic flux through a pipe wall. Each sensor head may include one or more sensors. The magnets may saturate a portion of pipeline to be inspected with an axial magnetic flux. The sensors may measure the magnetic flux and, in particular, may detect changes or aberrations in the magnetic flux. Defects in the pipeline, including corroded areas, areas missing metal, geometric deformations, dents, buckles, wrinkles, cracks, and the like may induce aberrations and changes into the magnetic flux, or the magnetic flux may leak at the particular location of a defect.

The axial magnetizers may travel through a pipe having an internal diameter less than the nominal diameter of the magnetizer and may be configured to closely articulate with the pipe wall. A pipe may have some structural aberration, such as a crack or crack-like anomaly. An axial magnetizer may be particularly adept at detecting circumferentially oriented aberrations or defects. The magnetic field from the magnets may be imparted to the pipe wall by front magnetic circuit pole and rear magnetic circuit pole (each having opposite polarities) to saturate the pipe wall with magnetic flux. Sensors may be placed between magnets to be within the magnetic field. The magnetic field may be disrupted when the axial magnetizers pass over aberrations or flaws, and the disruption in the magnetic flux may be detected by the sensors.

In an embodiment, a magnet bar may include a plurality of sensors between each magnetic circuit pole to measure the magnetic flux imparted into the pipe. The magnetic circuit poles may impart a magnetic flux into a pipe wall, and the magnetic flux may flow from one magnetic circuit pole to the other. Sensors positioned within the magnetic field may measure the magnetic flux. In an embodiment, sensors may be spaced at approximately 0.080 inches (2.0 mm). In an embodiment, sensors may comprise Hall-effect sensors. In an embodiment, an axial magnetizer may include six magnet bars and may have 40 Hall sensors per diameter-inch. Aberrations in the pipe may cause distortions or disruptions in the magnetic field, and the sensors may thus detect the irregularities in the magnetic field corresponding to the aberration in the pipe. A magnetizer utilizing an axially oriented magnetic field may be able to detect circumferential flaws of 0.8 inches (20 mm) with an opening of 0.004" (0.1 mm). A sensor head may be able to survive forces of up to about 20G, and sensors may be able to withstand pressures of up to 2,000 psi (13.8 Mpa) and velocities of up to 30 ft/s (9 m/s).

In an embodiment, each sensor head may include a plurality of sensors. The plurality of sensors may include Hall-effect sensors, eddy-current sensors, ultrasonic sensors (such as EMAT sensors), or combinations thereof. The responses of each sensor may be combined and analyzed to locate or define certain pipeline defects, as discussed above. For example, a Hall-effect sensor may detect a response to a magnetic field leakage. The output of a Hall-effect sensor may vary linearly or nonlinearly with respect to changes in the magnetic field. These changes may reflect the presence of a flaw, defect, or anomaly. The output of a plurality of such sensors, in the aggregate, may allow for an ultra-high resolution sampling in a given area of the internal pipe surface, thereby allowing defects to be accurately detected, characterized, analyzed, and quantified. In an embodiment, an axial magnetizer according to an aspect of the present disclosure may measure and store flux leakage values to a sampling density of up to 320 per square inch (50 square cm). In an embodiment, an axial magnetizer according to the present disclosure may include several sensor heads, each sensor head having a plurality of individual sensors. In an embodiment, a pig may include two axial magnetizer modules with six sensor heads per module and 24 Hall-effect sensors per sensor head. In an exemplary embodiment, a smart pig may have a diameter greater than six inches and contain two axial magnetizer modules, wherein each module includes six sensor heads. In an embodiment, an axial magnetizer may have a sensor density of between about 30 to 100 sensors per diameter-inch.

An axial magnetizer may be sized to have a nominal diameter slightly larger than the diameter of a pipe. For example, an axial magnetizer slightly larger than six inches in diameter may be configured to travel through a six-inch pipe. One of skill in the art will recognize that an axial magnetizer according to the present disclosure may be sized to inspect pipes of alternate diameters. An axial magnetizer may include compression features allowing the magnetizer to fit inside and travel within the pipe.

With reference back to FIG. 16, magnetic circuit poles 1603, 1604 may contact the interior of the pipeline. In an embodiment, magnetic circuit poles 1603, 1604 may function as a flux coupler to more efficiently saturate a pipe wall with a magnetic field. In a detailed embodiment, magnetic circuit poles 1603, 1604 may include wear pads 1702 on at least a portion of a surface that contacts the pipe wall. Wear pads 1702 may comprise one or more ceramic or carbide inserts 1703, as depicted in FIG. 17. Ceramic or carbide inserts 1703 may protect the magnetic circuit poles 1603, 1604 from wear and may reduce drag force. In an embodiment, ceramic or carbide inserts 1703 may reduce drag force by about 30%.

Sensor head wear pad 1702 may comprise a nickel-based alloy or superalloy. Magnetic circuit poles 1603, 1604 may include a ceramic insert 1703 or coating. In detailed embodiments, the ceramic may comprise silicon carbide. In alternate detailed embodiments, the inserts may comprise tungsten carbide. Other varieties will be apparent to those skilled in the art.

Figure 18:
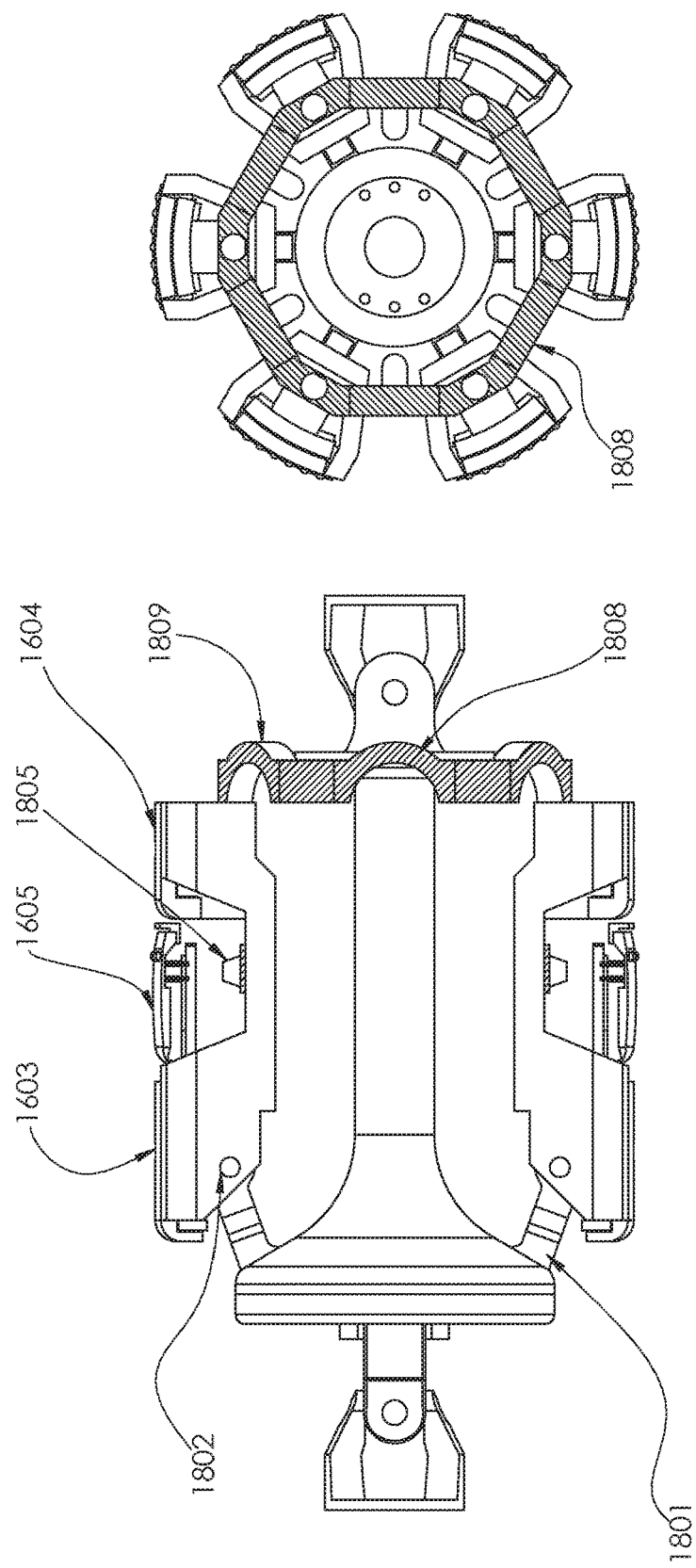
FIG. 18 shows a side view of an embodiment of an axial magnetizer with a magnet bar removed to illustrate certain features.

The axial magnetizer according to the embodiment depicted in FIG. 18 may include a means for collapsing the magnet bars. Means for collapsing may comprise front links 1801 and torsion spring 1802. Torsion spring 1802 may exert a sufficient force, such as a spring force, to maintain the magnetic circuit poles 1603, 1604 in engagement with the pipe wall but may collapse, entirely or partially, if the magnetic circuit poles 1603, 1604 encounter an aberration in the pipe, such as an indentation, or if the pig including the axial magnetizer encounters a bend in the pipe. In an embodiment, sensor head 1605 is also operatively coupled to the means for collapsing by virtue of it being part of the magnet bar. In an alternate embodiment, sensor head 1605 includes an independent sensor head suspension system. Sensor head suspension system may include one or more conical springs 1805 coupling the bottom of the sensor head 1605 to the magnet bar. In an embodiment, sensor head suspension system comprises dual conical springs 1805. Both means for collapsing and sensor head suspension system may enable components of the axial magnetizer to collapse up to 25% of the outside diameter of the pipe; that is, the diameter of at least part of the axial magnetizer may be reduced by up to 25% when encountering an aberration in the pipe or when going around a bend in the pipeline. These features may allow a pig to navigate pipeline bends of greater than or equal to 1.5 D (where D is equal to the pipe diameter). In an embodiment, these features may allow a pig to navigate pipeline bends with a minimum separation of 2D (i.e., two pipe diameters separation). In another embodiment, the features may allow a pig to navigate a pair of 1.5D bends separated from each other by a pipeline distance equal to 3D. The collapsibility features may reduce drag force on the axial magnetizer, which may help to prevent a pig from stalling when navigating a relatively tight bend.

In an embodiment, each magnet bar may include rear links similar to links 1801 to join the rear end of each magnet bar to the central shaft, along with a torsion spring. Such an embodiment may maintain the entire magnet bar in contact with the pipe wall. Alternatively, each magnet bar of an axial magnetizer may include a front control link 1801 and a torsion spring 1802. Torsion spring 1802 may support the weight of each magnet bar and may help to support the weight of the central shaft. The rear portion of the axial magnetizer may include a polyurethane ring 1808. Polyurethane ring 1808 may help to maintain each magnet bar biased against the pipe wall but may also help to balance forces, especially when encountering aberrations in the pipeline or when navigating bends. Polyurethane ring 1808 may include bends 1809, which may allow polyurethane ring 1808 to temporarily collapse and allow the magnet bar(s) to collapse toward the center shaft. Ring 1808 may be made from polyurethane for durability and chemical resistance concerns; however, one of skill in the art may recognize alternative materials from which ring 1808 may be constructed, such as silicone or a durable, chemical-resistant thermoplastic.

A sensor head may be in the shape of a sloping trapezoid. The approach angle of a sensor head according to such a design may minimize the transmission of mechanical shocks and vibrations to the sensors and electronics. Furthermore, such a sensor head design may provide a longer wear life, which may contribute to a longer inspection time of a smart pig between repairs. In an embodiment, one or more sensor heads may extend radially outward and articulate with a surface of a pipeline to track the pipeline surface. In an alternate embodiment, sensor head may be shaped as a parallelogram or a rhomboid.

Figure 19:
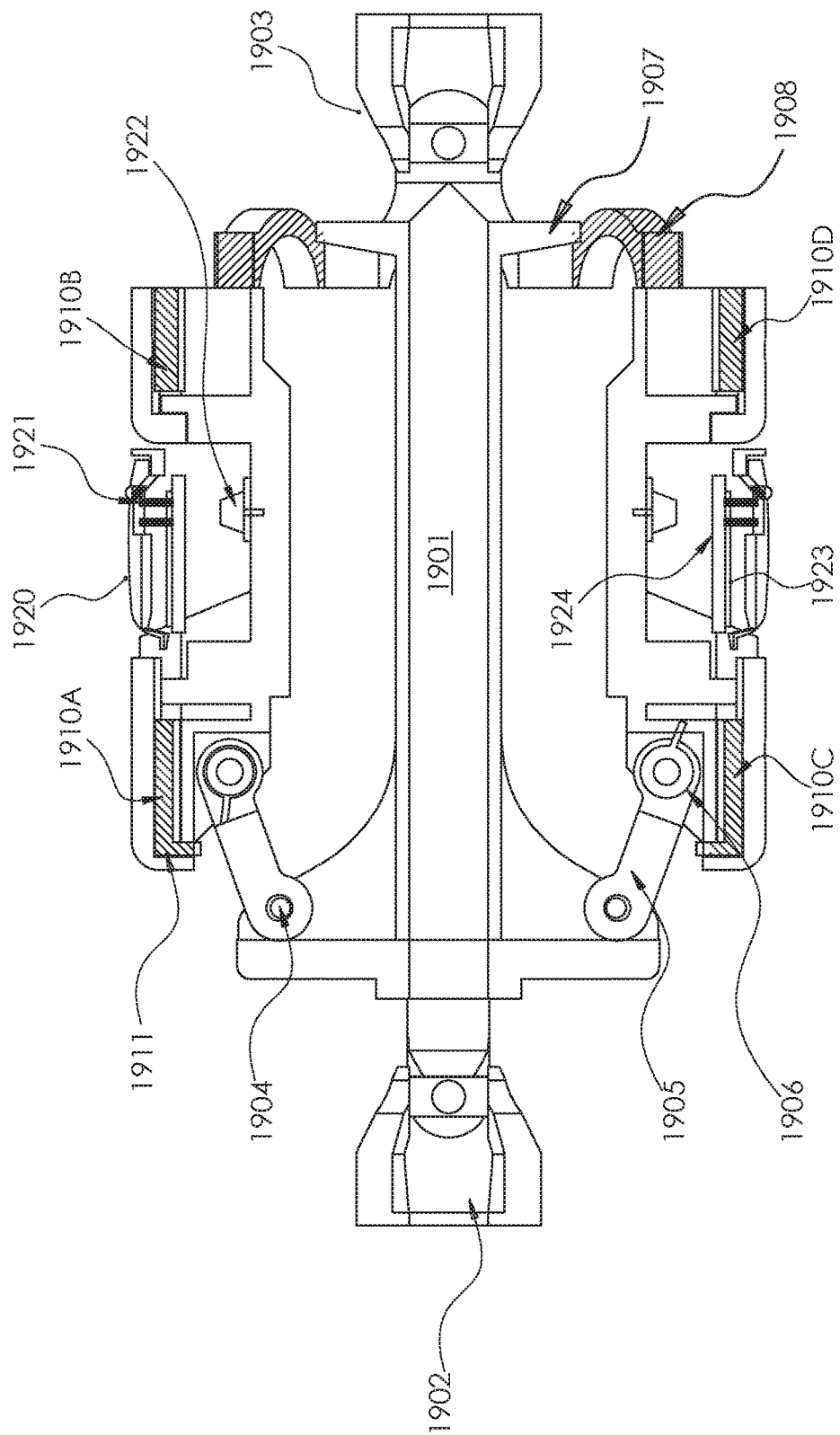
FIG. 19 a cross-section of a side view of an axial magnetizer in accordance with an embodiment of the present disclosure.

FIG. 19 presents a cross-sectional side view of an embodiment of an axial magnetizer. The embodiment of FIG. 19 may include a central shaft 1901 running approximately through the axial magnetizer's central axis and providing a central support for other elements. A front universal joint 1902 and a rear universal joint 1903 may be coupled to respective ends of the central shaft 1901. Front universal joint 1902 and rear universal joint 1903 may couple the axial magnetizer to one or more other modules of a pig, such as another axial magnetizer, an electronics module, a mapping module, a circumferential magnetizer, or the like. In an embodiment, front universal joint 1902 and rear universal joint 1903 may be able to rotate about central shaft 1901. In an embodiment, central shaft 1901 may extend to universal joint limiter 1907, which may limit the movement of the universal joints 1902, 1903. For example, if two axial magnetizers connected by universal joints have a limited rotational movement, the magnetizers may maintain a consistent orientation with respect to each other to maintain 360-degree pipe wall coverage. Front universal joint 1902 and rear universal joint 1903 may be coupled to central shaft 1901 by a bolt or similar coupling mechanism, about which the universal joints 1902, 1903 may pivot. The ability of universal joints 1902, 1903 to pivot may allow the pig, including the axial magnetizer, to better navigate sharper bends in the pipeline. For example, a pig including an axial magnetizer according to the embodiment described in FIG. 19 may be capable of negotiating a 3D (where D is equal to the nominal pipe diameter) pipe bend radius. In another example, the pig may be able to navigate a pair of 1.5D bends separated from each other by a pipeline distance equal to 3D.

An axial magnetizer according to an embodiment such as that illustrated in FIG. 19 may include one or more magnet bars. In an embodiment, an axial magnetizer may include six magnet bars, each providing approximately 30 degrees of pipe wall coverage. Each magnet bar may be coupled to the center shaft 1901 at the front end with a magnet bar link 1905 at magnet-bar-to-center-shaft connection 1904. Connection 1904 may include a bolt (or other similar coupling mechanism) about which magnet bar link 1905 may rotate or pivot. The ability of the magnet bar to rotate or pivot about connection 1904 may allow the magnet bar to collapse toward the center shaft 1901. In an embodiment, the collapsibility of each magnet bar may allow an axial magnetizer to reduce its cross-sectional diameter by about 25%. This may allow the magnetizer to navigate tighter turns than would otherwise be possible without becoming stuck or stalled. Without becoming stalled around a bend, a pig with an axial magnetizer according to the present disclosure may be able to maintain more consistent speed—even around tight bends—and thus may maintain more a more complete measurement of the pipeline. In contrast, if a pig stalls around a bend, pressure may build up behind the pig, eventually shooting the pig forward through the bend at a velocity that is too high to take measurements of the pipeline, thus reducing the quality of the inspection. A torsion spring 1906 may be included at the connection between the magnet bar and the magnet bar link 1905 to support the weight of the magnet bar and to maintain the magnet bar in a biased position against the pipe wall, while still allowing for collapsibility when necessary. In an embodiment, a polyurethane ring 1908 may couple the rear end of the magnet bar to the center shaft 1901. Polyurethane ring 1908 may include an outward bend (e.g., a rearward-facing bend), which may allow the magnet bar to collapse toward the center shaft when encountering a sufficient force (e.g., a pipe aberration or bend). Polyurethane ring 1908 may also absorb shock.

Each magnet bar may include front magnet(s) 1910A. Front magnet(s) 1910A may have a first polarity. Each front magnet 1910A has the same polarity as the other front magnets, such as front magnet(s) 1910C. Rear magnet(s) 1910B may have the opposite polarity as front magnet 1910A. Each rear magnet 1910B had the same polarity as the other rear magnets, such as rear magnet(s) 1910D. Each magnet bar may include one or more magnet shields 1911. Magnet shields 1911 may help to focus the magnetic field from the magnets to allow more efficient transfer of magnetic flux through the pipe wall and, accordingly, more consistent, accurate, and efficient measurements to be taken. Each magnet bar may include a sensor head 1920, which may include a wear pad, upon which Hall effect sensors 1921 may be disposed. Sensor head may further include a sensor board 1923 and a sensor head base plate 1924. For example, sensor board 1923 may be a printed circuit board providing support and electrical connectivity to Hall effect sensors 1921. Each sensor head 1920 may include one or more conical springs 1922 coupling the sensor head 1920 to the magnet bar. In an embodiment, each sensor head 1920 is coupled to its respective magnet bar by dual conical springs 1922. Conical springs 1922 may support the sensor head 1920, may keep the sensor head positioned against a pipe wall, and may allow for collapsibility when encountering an aberration or bend in the pipeline.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A circumferential magnetizer module for a smart pig, comprising:
    a central shaft; and
    at least one magnet bar, coupled to the central shaft by a means for collapsing, and configured to induce a magnetic field transverse to a longitudinal axis of the central shaft to a pipe wall, the at least one magnet bar comprising:
        at least one magnet comprising a north pole side and a south pole side;
        a north magnetic circuit pole coupled to the north pole side of the at least one magnet and extending radially away from the central shaft;
        a south magnetic circuit pole coupled to the south pole side of the at least one magnet and extending radially away from the central shaft; and
        a sensor head to monitor magnetic flux comprising at least one sensor disposed between the north magnetic circuit pole and the south magnetic circuit pole.
2. The circumferential magnetizer module of claim 1, wherein the means for collapsing comprises a torsion spring to allow the magnet bar to move radially inward toward the central shaft.

3. The circumferential magnetizer module of claim 2, wherein the circumferential magnetizer module has a diameter about 25% smaller when the means for collapsing is fully compressed.

4. The circumferential magnetizer module of claim 1, further comprising six magnet bars.

5. The circumferential magnetizer module of claim 1, wherein the north magnetic circuit pole and the south magnetic circuit pole include a plurality of wear pads.

6. The circumferential magnetizer module of claim 5, wherein the wear pads are ceramic or tungsten carbide inserts.

7. The circumferential magnetizer module of claim 1, wherein the at least one sensor includes one or more of: a Hall-effect sensor and an ultrasonic sensor.

8. The circumferential magnetizer module of claim 1, wherein the sensor head has a sloping trapezoid, rhomboid, rectangle, or parallelogram shape.

9. The circumferential magnetizer module of claim 1, wherein the sensor head further comprises a suspension system comprising at least one conical spring to position the sensor head during operation.

10. The circumferential magnetizer module of claim 1, further comprising a joint extending axially from the central shaft to link an additional module of the smart pig.

11. The circumferential magnetizer module of claim 1, wherein the at least one magnet is a rare earth magnet.

12. A smart pig, comprising:
a plurality of circumferential magnetizers, each circumferential magnetizer comprising:
a central shaft; and
at least one magnet bar, coupled to the central shaft by a means for collapsing, and configured to induce a magnetic field transverse to a longitudinal axis of the central shaft to a pipe wall, the at least one magnet bar comprising:
at least one magnet comprising a north pole side and a south pole side;
a north magnetic circuit pole coupled to the north pole side of the at least one magnet and extending radially away from the central shaft;
a south magnetic circuit pole coupled to the south pole side of the at least one magnet and extending radially away from the central shaft; and
a sensor head to monitor magnetic flux comprising at least one sensor disposed between the north magnetic circuit pole and the south magnetic circuit pole.

13. The smart pig of claim 12, further comprising three circumferential magnetizers.

14. The smart pig of claim 13, wherein each circumferential magnetizer includes six magnet bars coupled to and disposed evenly about the central shaft, and wherein each magnet bar provides approximately 20 degrees of pipe wall coverage.

15. The smart pig of claim 12, wherein each circumferential magnetizer includes six magnet bars.

16. The smart pig of claim 14, wherein the circumferential magnetizers are configured to provide 360 degrees of pipe wall coverage.

* * * * *